United States Patent
Halseth et al.

(10) Patent No.: US 7,329,238 B2
(45) Date of Patent: Feb. 12, 2008

(54) SAFETY NEEDLE MEDICAL BEARING DEVICES

(75) Inventors: Thor R. Halseth, Agoura, CA (US); John Barker, Ventura, CA (US); Michael J. Botich, Oxnard, CA (US)

(73) Assignee: Specialized Health Products Inc., Bountiful, UT (US)

( * ) Notice: Subject to any disclaimer, the term of this patent is extended or adjusted under 35 U.S.C. 154(b) by 238 days.

(21) Appl. No.: 10/149,172

(22) PCT Filed: Dec. 7, 2000

(86) PCT No.: PCT/US00/33436

§ 371 (c)(1),
(2), (4) Date: Dec. 2, 2003

(87) PCT Pub. No.: WO01/45776

PCT Pub. Date: Jun. 28, 2001

(65) Prior Publication Data

US 2004/0116853 A1   Jun. 17, 2004

Related U.S. Application Data

(60) Provisional application No. 60/169,430, filed on Dec. 7, 1999.

(51) Int. Cl.
*A61M 5/00* (2006.01)
(52) U.S. Cl. ...................................... 604/110
(58) Field of Classification Search ............... 604/110, 604/181, 187, 188, 192–198, 263
See application file for complete search history.

(56) References Cited

U.S. PATENT DOCUMENTS

| | | |
|---|---|---|
| 2,876,770 A | 3/1959 | White |
| 3,306,290 A | 2/1967 | Weltman |
| 3,463,152 A | 8/1969 | Sorenson |
| 3,658,061 A | 4/1972 | Hall |
| 3,890,971 A | 6/1975 | Leeson et al. |
| 4,026,287 A | 5/1977 | Haller |
| 4,333,457 A | 6/1982 | Margulies |
| 4,378,015 A | 3/1983 | Wardlaw |
| 4,392,859 A | 7/1983 | Dent |
| 4,425,120 A | 1/1984 | Sampson et al. |
| 4,507,117 A | 3/1985 | Vining et al. |
| 4,507,118 A | 3/1985 | Dent |
| 4,542,749 A | 9/1985 | Caselgrandi et al. |
| 4,573,976 A | 3/1986 | Sampson et al. |
| 4,592,744 A | 6/1986 | Jagger et al. |
| 4,631,057 A | 12/1986 | Mitchell |

(Continued)

FOREIGN PATENT DOCUMENTS

| | | |
|---|---|---|
| EP | 0 565 882 | 10/1993 |
| EP | 0 704 225 | 9/1995 |

*Primary Examiner*—Matthew F. Desanto
(74) *Attorney, Agent, or Firm*—Paul S. Evans; Kevin Laurence

(57) ABSTRACT

The present invention relates to a syringe (10) for administering injections of medicinal fluids to a patient or withdrawal of fluid, such as blood from a patient. More specifically the present invention is a syringe device (10) for injecting medication or withdrawing fluid, wherein after use the needle (60) is shielded (15) against inadvertent contact to prevent needle sticks.

12 Claims, 24 Drawing Sheets

U.S. PATENT DOCUMENTS

| | | | | |
|---|---|---|---|---|
| 4,664,654 A | | 5/1987 | Strauss | |
| 4,675,005 A | | 6/1987 | DeLuccia | |
| 4,692,156 A | | 9/1987 | Haller | |
| 4,710,170 A | | 12/1987 | Haber et al. | |
| 4,723,943 A | | 2/1988 | Spencer | |
| 4,725,267 A | | 2/1988 | Vaillancourt | |
| 4,737,144 A | | 4/1988 | Choksi | |
| 4,747,831 A | | 5/1988 | Kulli | |
| 4,767,413 A | | 8/1988 | Haber et al. | |
| 4,770,655 A | | 9/1988 | Haber et al. | |
| 4,804,371 A | | 2/1989 | Vaillancourt | |
| 4,813,426 A | | 3/1989 | Haber et al. | |
| 4,828,548 A | | 5/1989 | Walter | |
| 4,838,863 A | | 6/1989 | Allard et al. | |
| 4,838,869 A | | 6/1989 | Allard | |
| 4,850,968 A | | 7/1989 | Romano | |
| 4,863,435 A | | 9/1989 | Sturman et al. | |
| 4,874,382 A | | 10/1989 | Lindemann et al. | |
| 4,887,998 A | | 12/1989 | Martin et al. | |
| 4,894,055 A | | 1/1990 | Sudnak | |
| 4,898,589 A | | 2/1990 | Dolgin et al. | |
| 4,900,307 A | | 2/1990 | Kulli | |
| 4,906,236 A | | 3/1990 | Alberts et al. | |
| 4,911,693 A | | 3/1990 | Paris | |
| 4,917,673 A | | 4/1990 | Coplin | |
| 4,921,486 A | | 5/1990 | DeChellis et al. | |
| 4,927,414 A | | 5/1990 | Kulli | |
| 4,927,416 A | | 5/1990 | Tomkiel | |
| 4,929,237 A | | 5/1990 | Medway | |
| 4,931,040 A | * | 6/1990 | Haber et al. | 604/110 |
| 4,932,947 A | | 6/1990 | Cardwell | |
| 4,946,446 A | | 8/1990 | Vadher | |
| 4,955,868 A | | 9/1990 | Klein | |
| 4,955,869 A | | 9/1990 | Bin | |
| 4,955,870 A | | 9/1990 | Ridderheim et al. | |
| 4,966,592 A | | 10/1990 | Burns et al. | |
| 4,966,593 A | | 10/1990 | Lennox | |
| 4,973,316 A | | 11/1990 | Dysarz | |
| 4,978,340 A | * | 12/1990 | Terrill et al. | 604/195 |
| 4,988,339 A | | 1/1991 | Vadher | |
| 4,994,034 A | | 2/1991 | Botich et al. | |
| 5,017,187 A | | 5/1991 | Sullivan | |
| 5,019,044 A | | 5/1991 | Tsao | |
| 5,046,508 A | | 9/1991 | Weissler | |
| 5,049,133 A | | 9/1991 | Villen Pascual | |
| 5,053,010 A | * | 10/1991 | McGary et al. | 604/110 |
| 5,064,419 A | | 11/1991 | Gaarde | |
| 5,084,018 A | | 1/1992 | Tsao | |
| 5,129,884 A | | 7/1992 | Dysarz | |
| 5,188,599 A | | 2/1993 | Botich et al. | |
| 5,269,761 A | * | 12/1993 | Stehrenberger et al. | 604/110 |
| 5,395,337 A | * | 3/1995 | Clemens et al. | 604/110 |
| 5,407,431 A | | 4/1995 | Botich et al. | |
| 5,487,732 A | * | 1/1996 | Jeffrey | 604/110 |
| 5,685,863 A | | 11/1997 | Botich et al. | |
| 5,788,677 A | | 8/1998 | Botich et al. | |
| 5,800,395 A | | 9/1998 | Botich et al. | |
| 5,868,713 A | * | 2/1999 | Klippenstein | 604/195 |
| 5,882,342 A | * | 3/1999 | Cooper et al. | 604/195 |
| 5,980,494 A | * | 11/1999 | Malenchek et al. | 604/198 |
| 6,039,713 A | * | 3/2000 | Botich et al. | 604/110 |
| 6,096,005 A | | 8/2000 | Botich et al. | |
| 6,179,812 B1 | | 1/2001 | Botich et al. | |
| 6,558,357 B1 | * | 5/2003 | Hoeck | 604/195 |

* cited by examiner

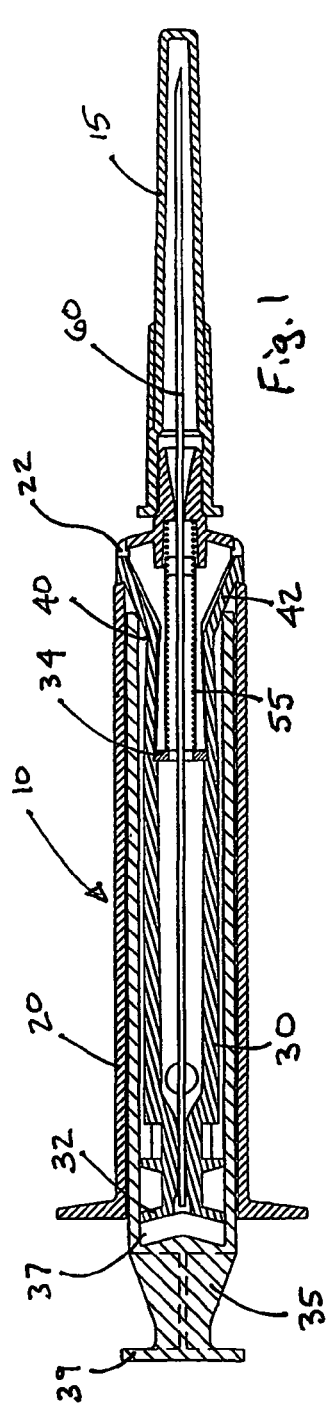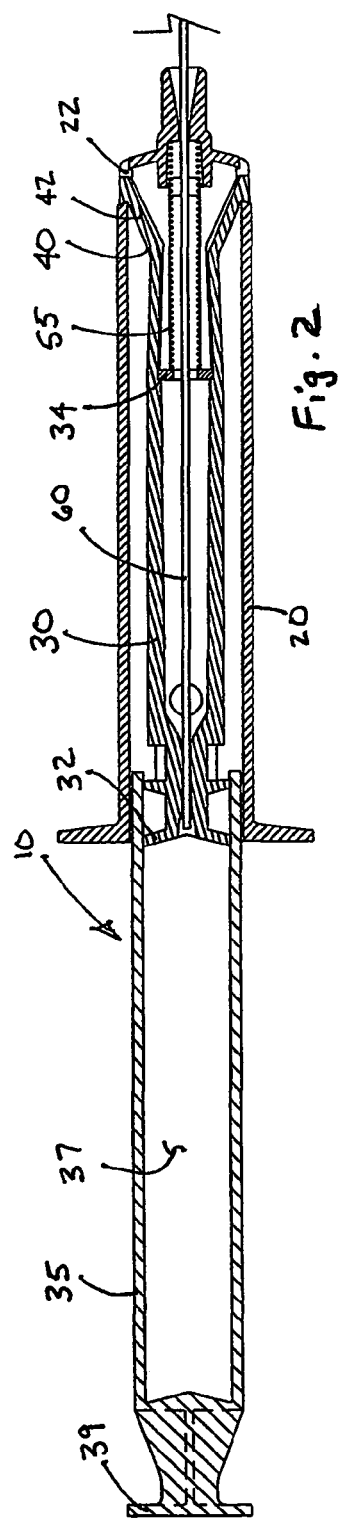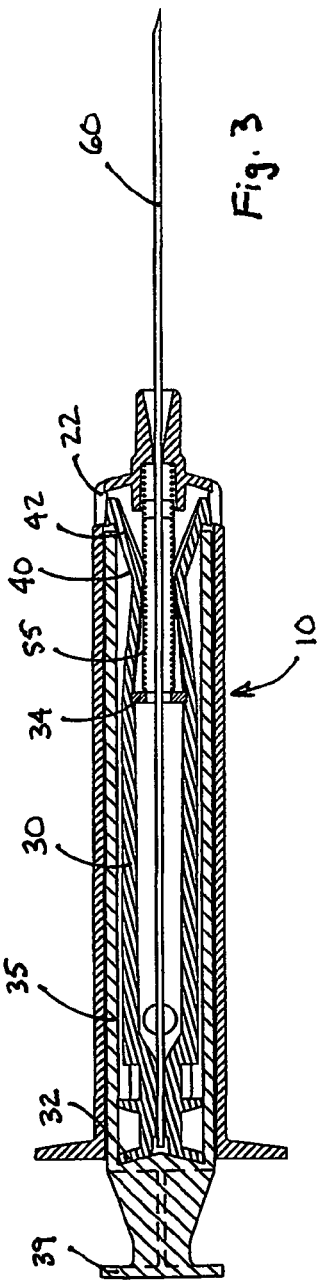

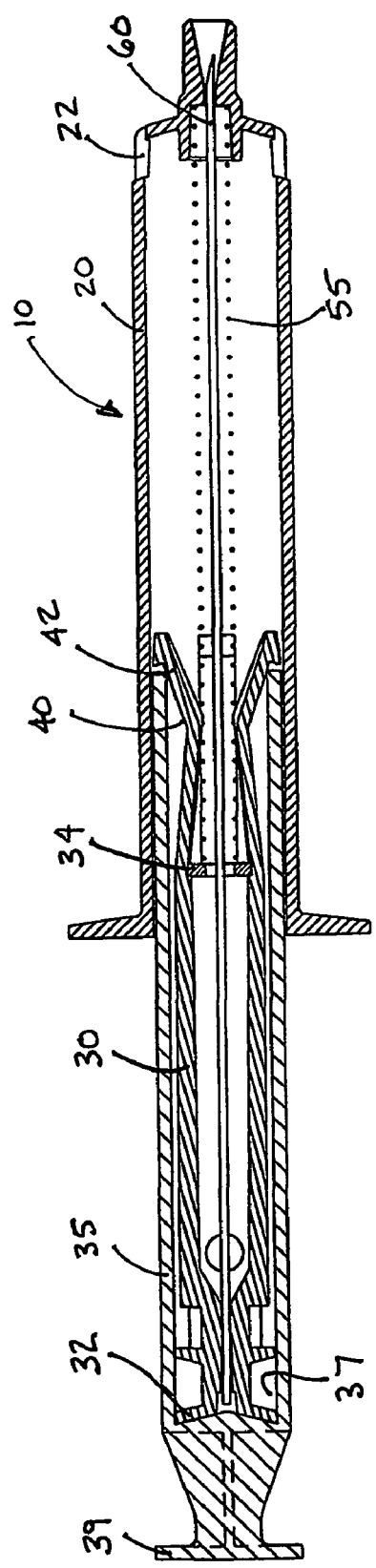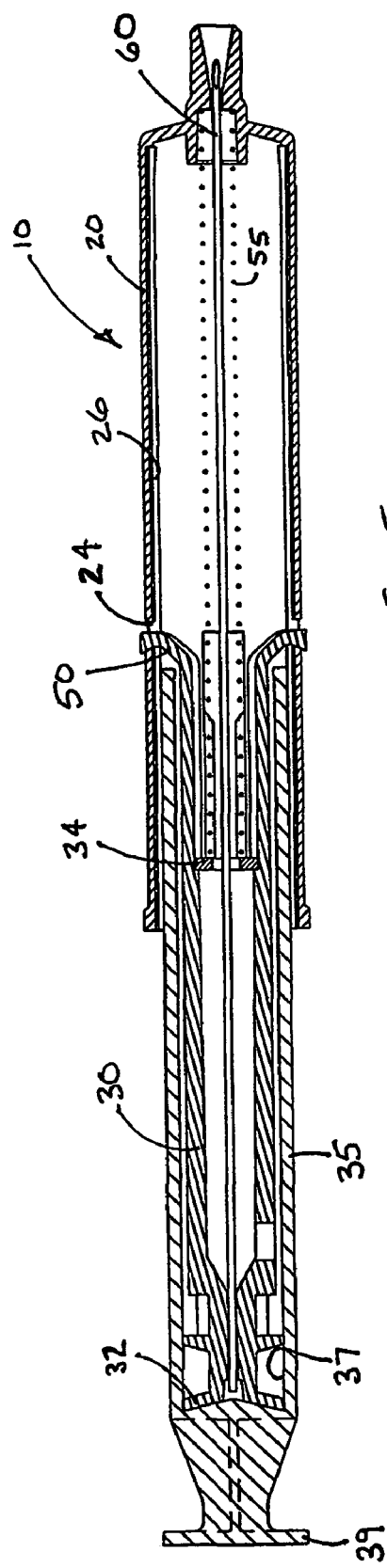

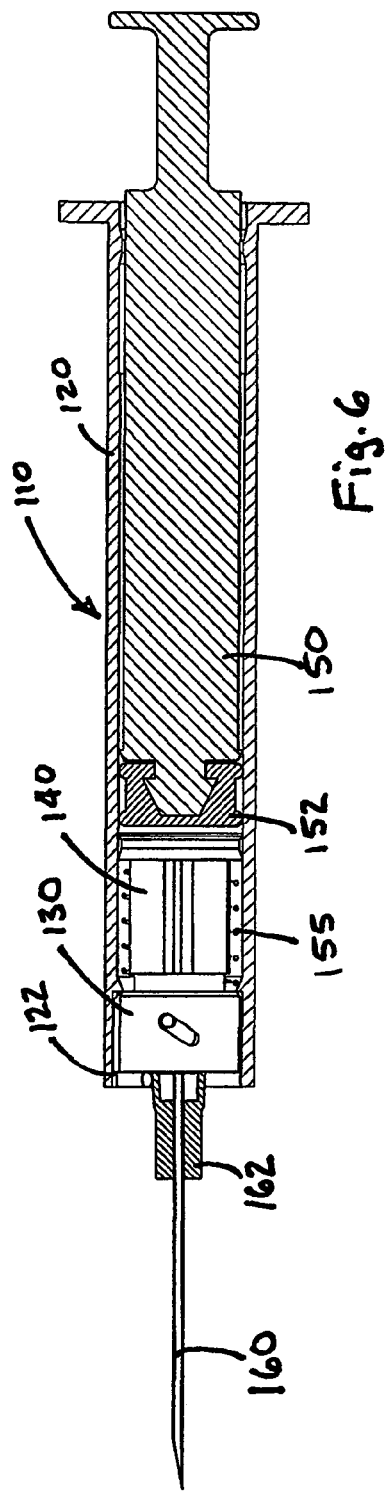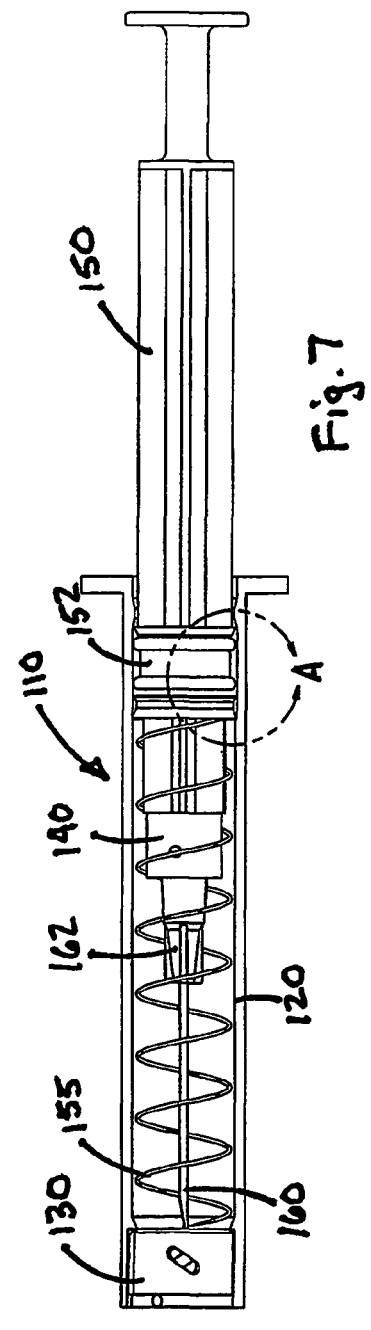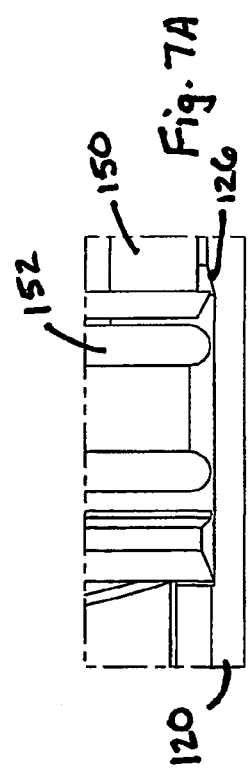

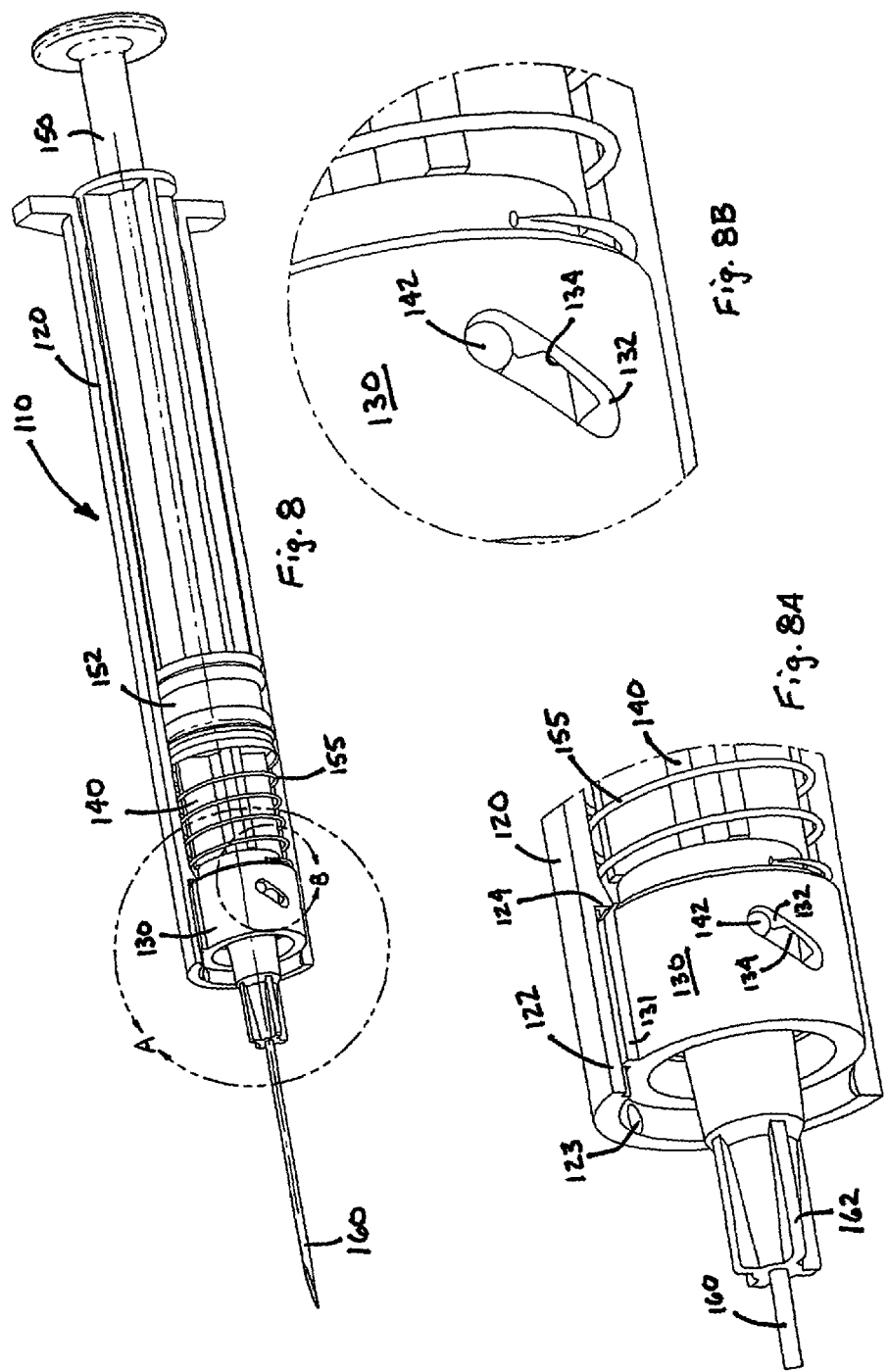

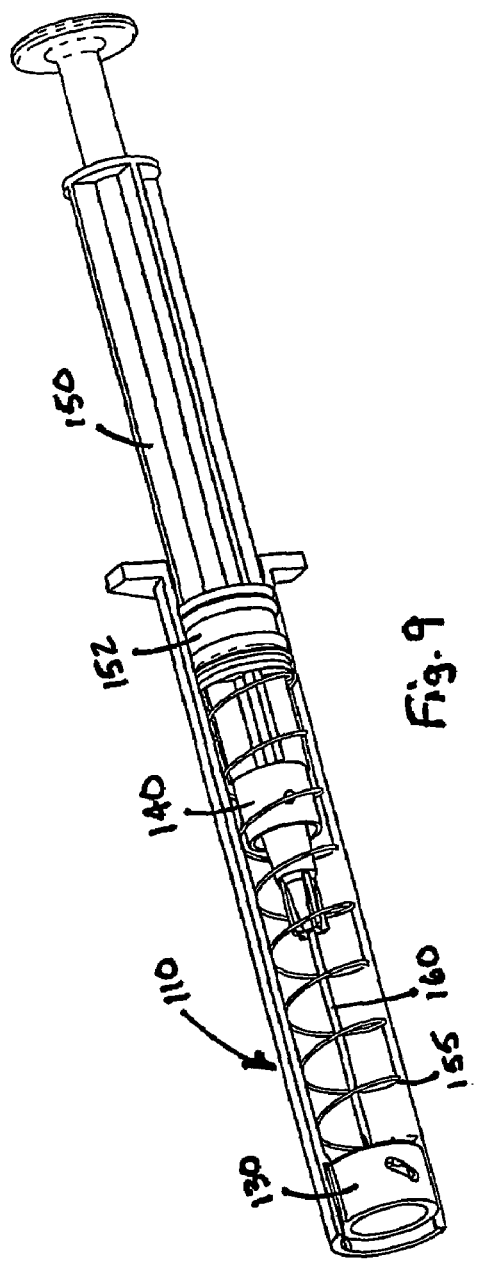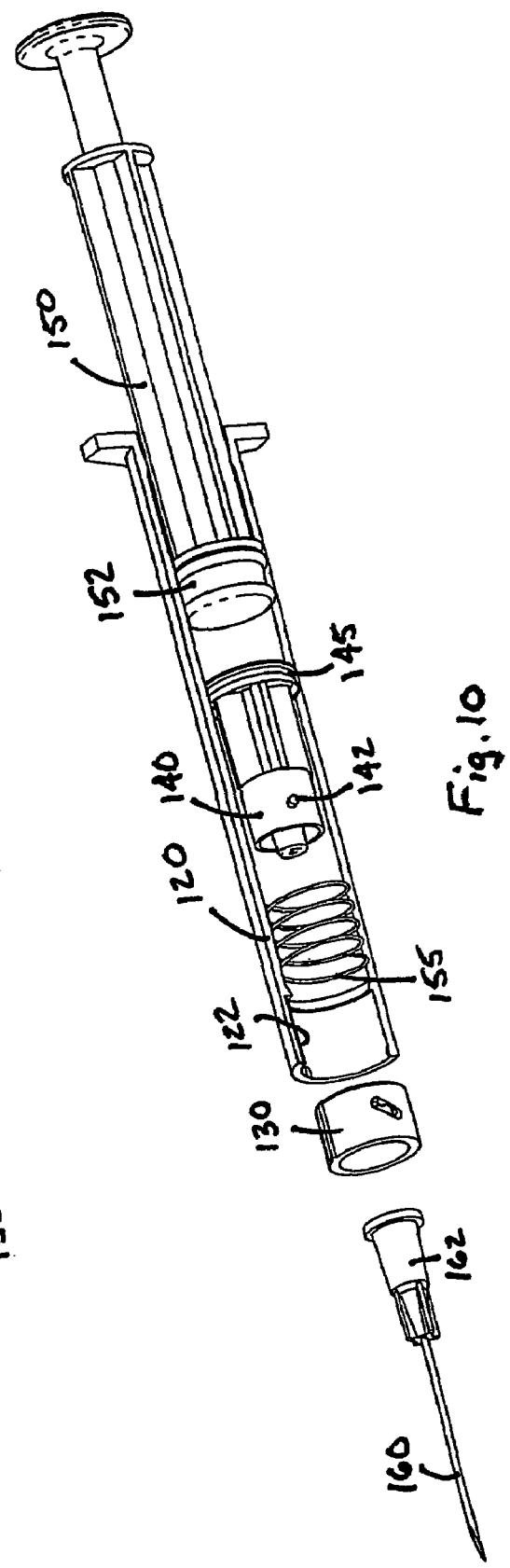

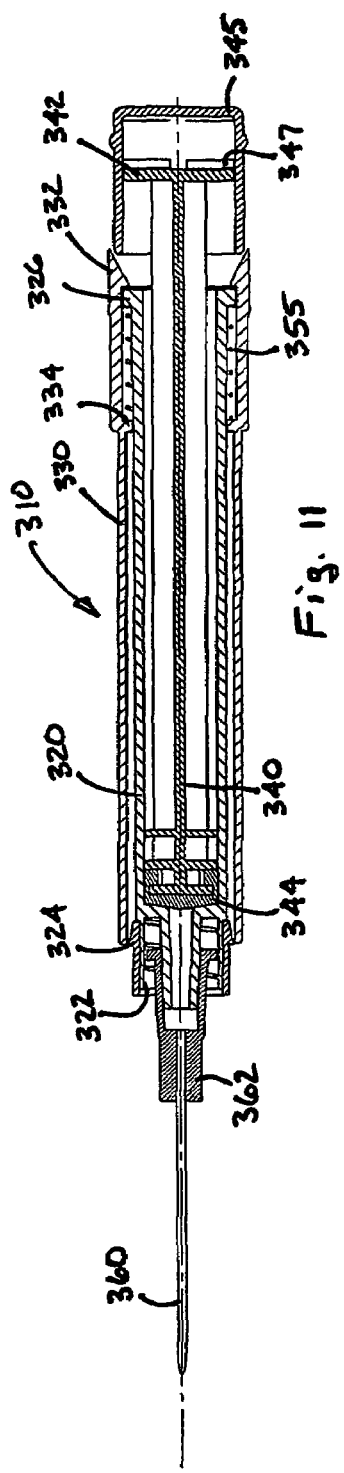
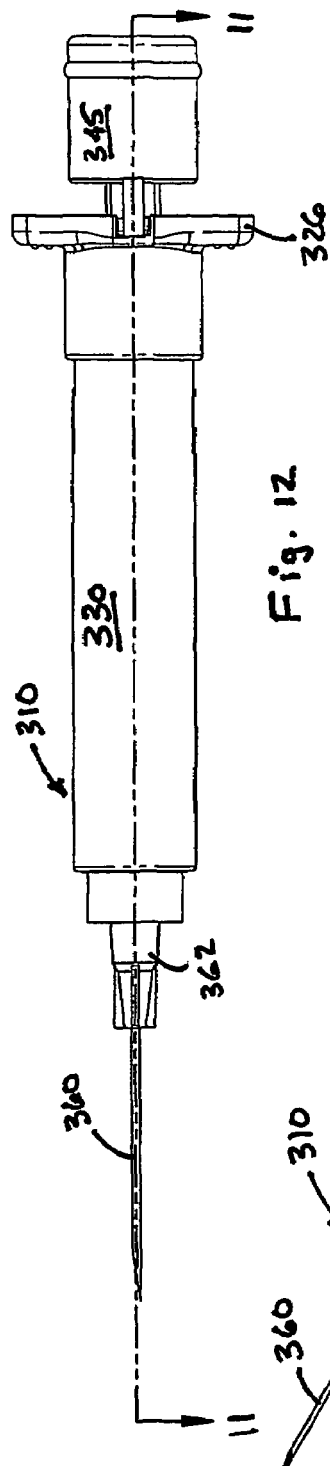
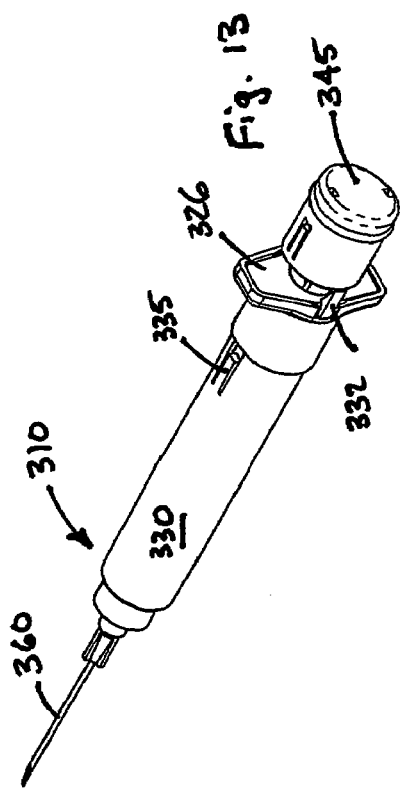

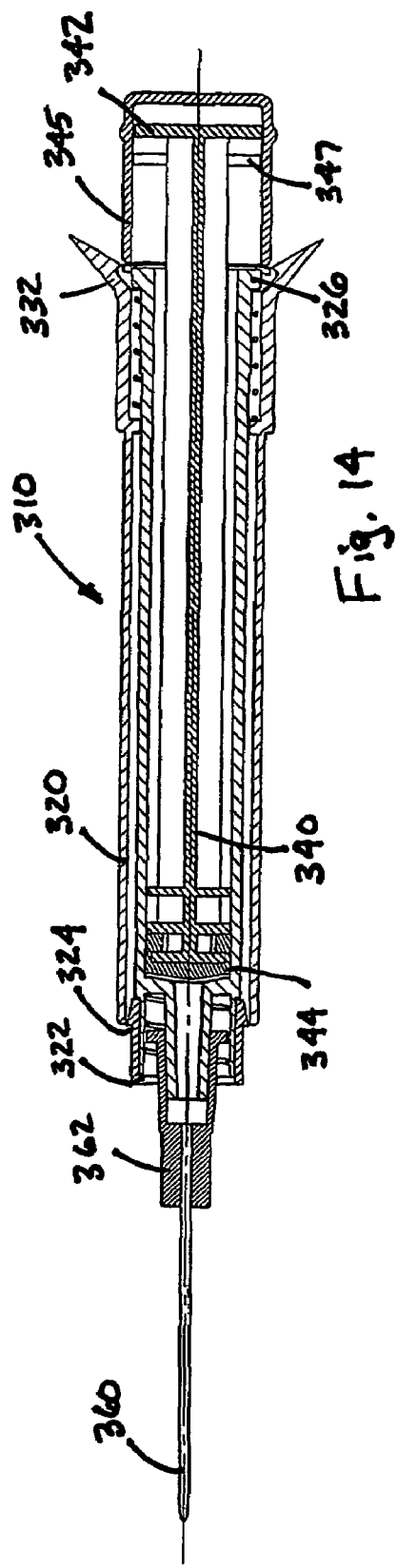
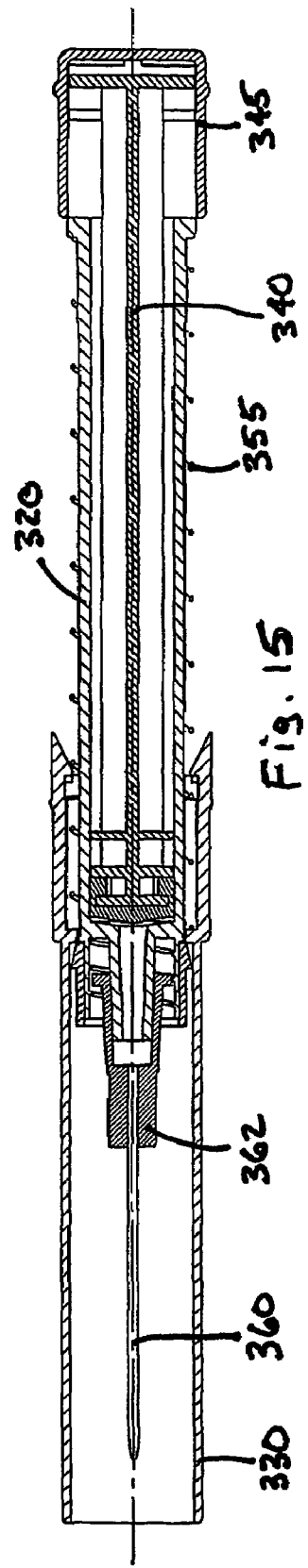

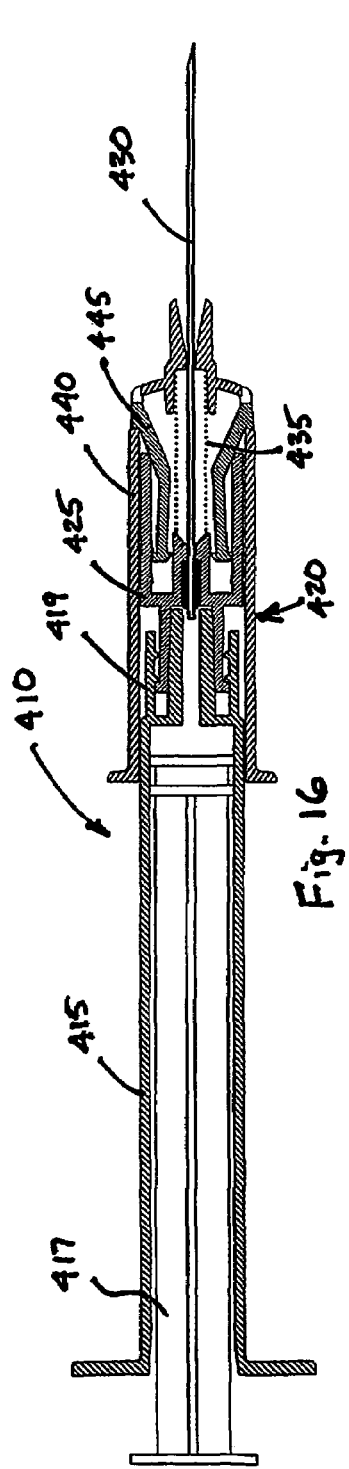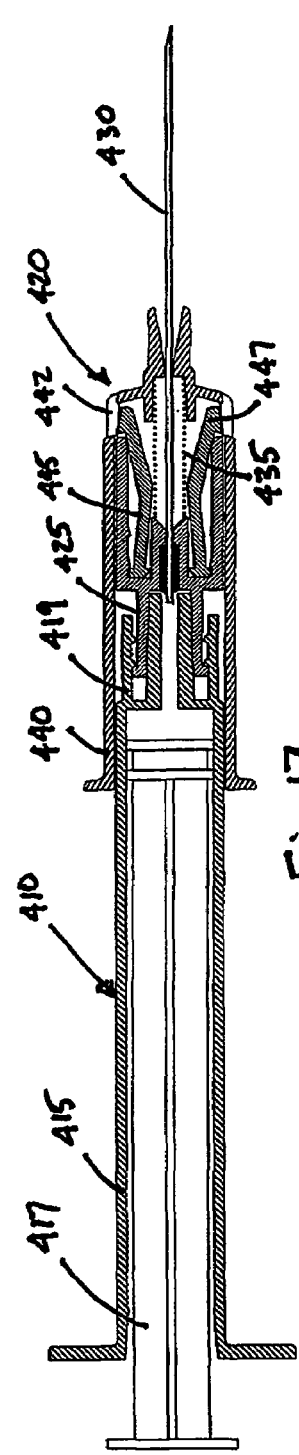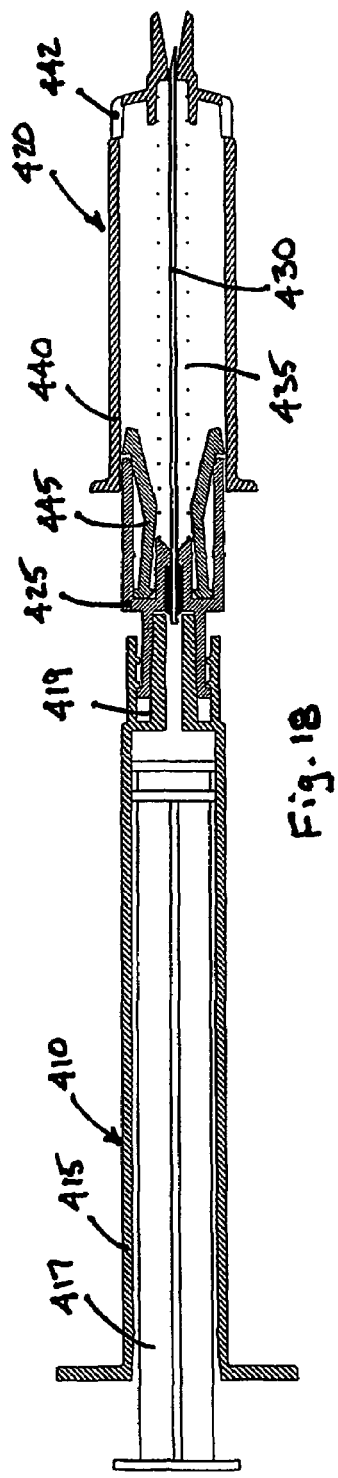

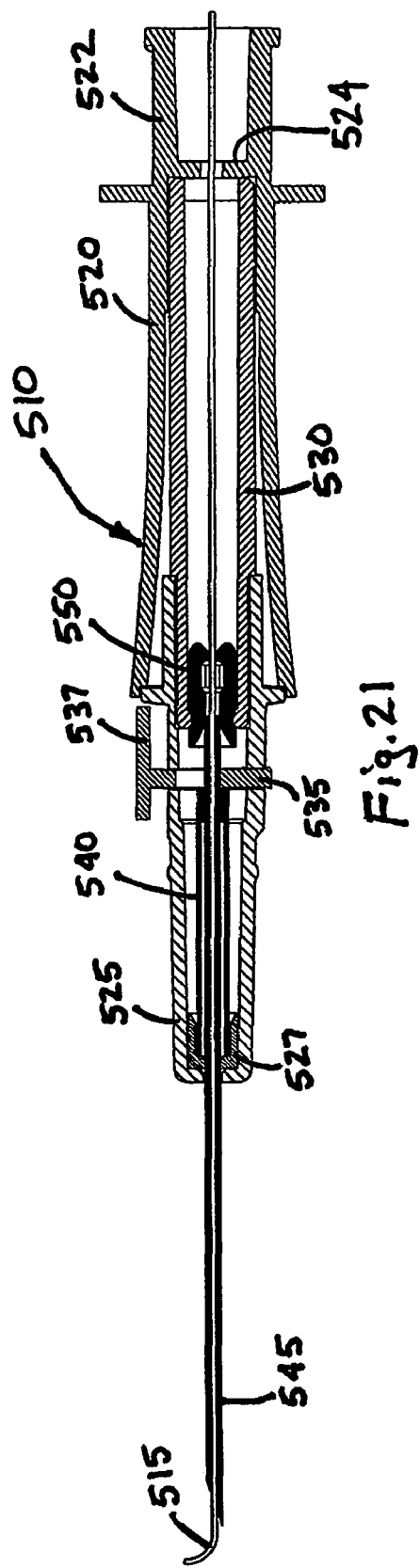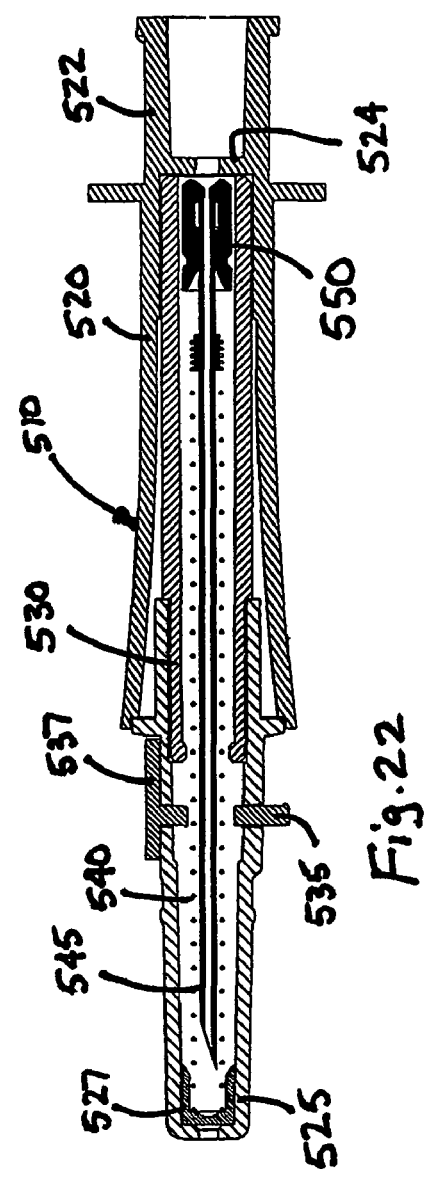

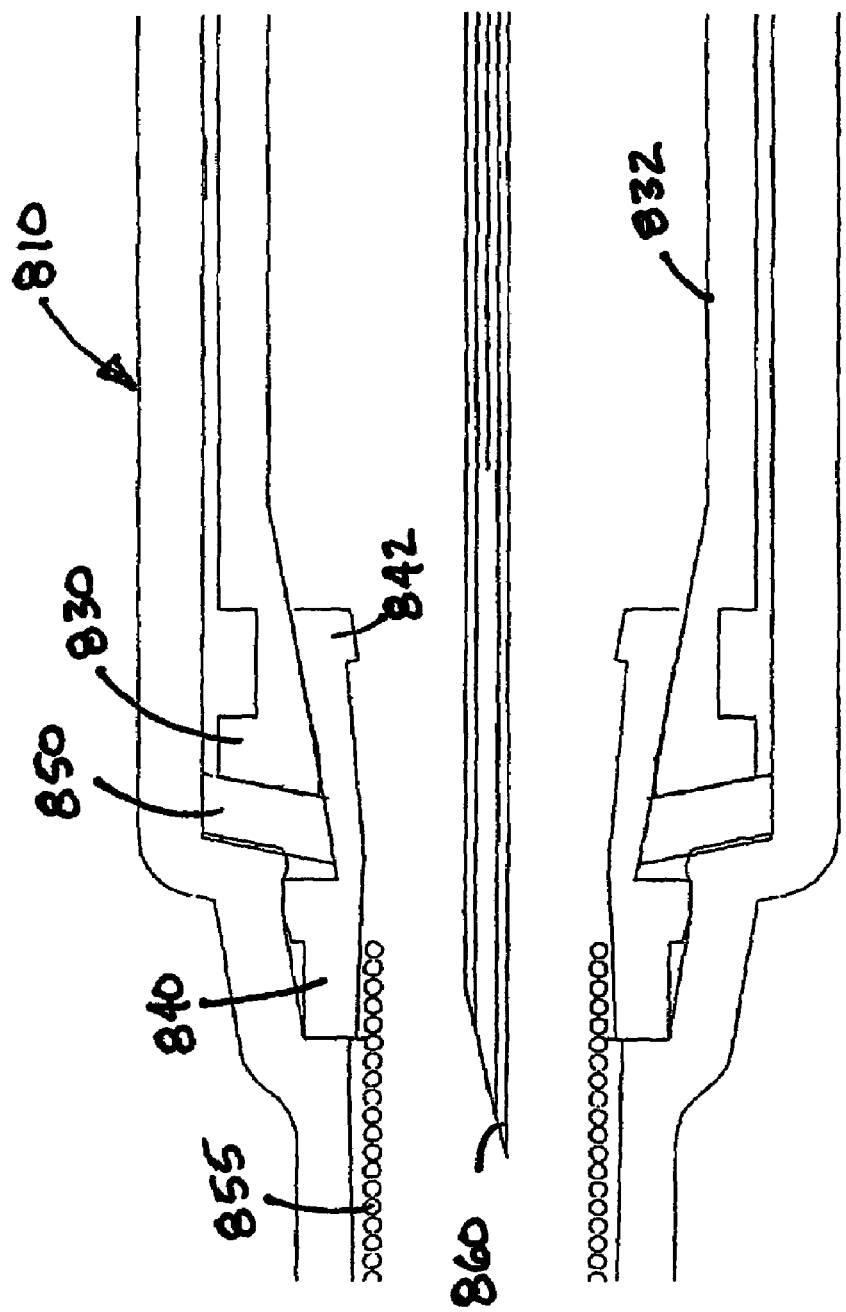

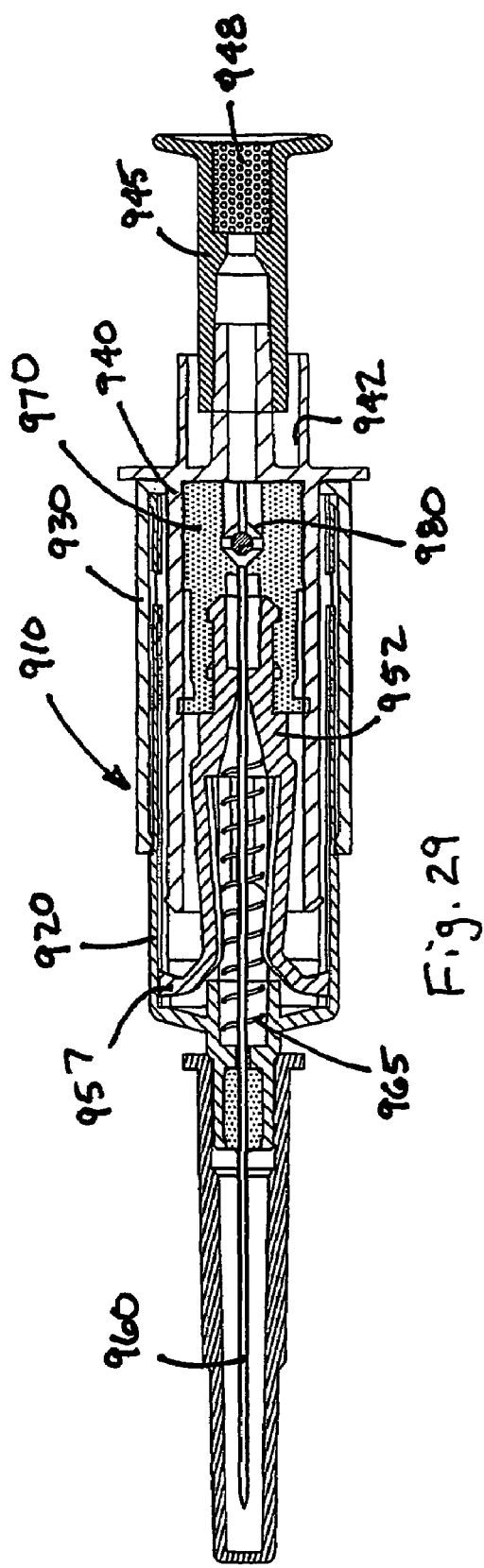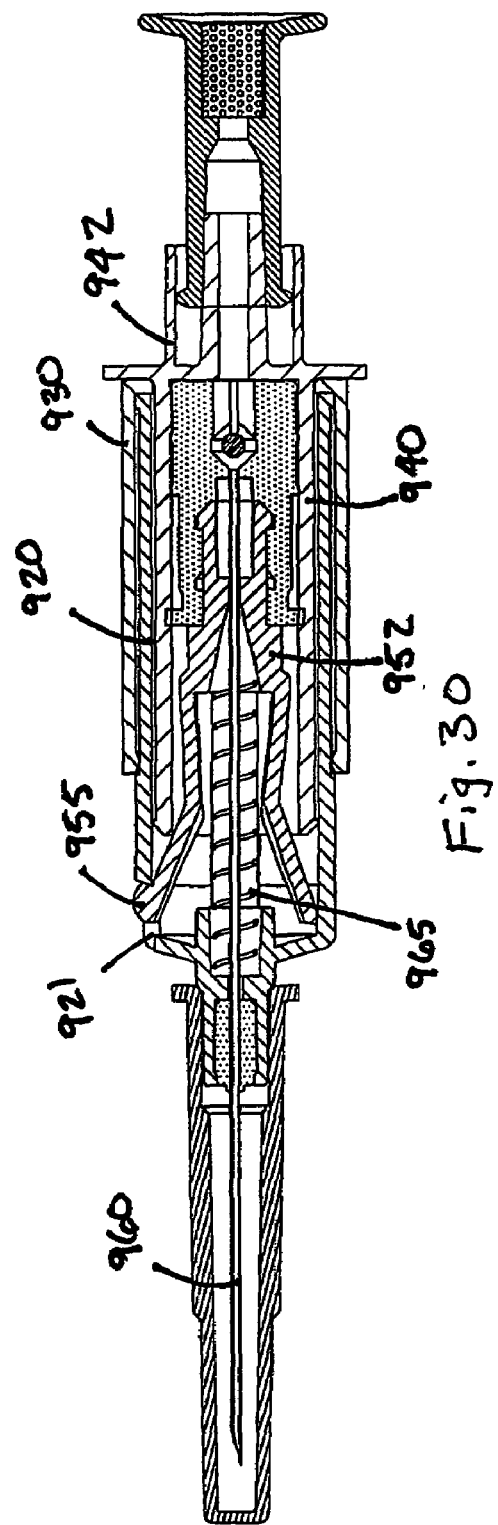

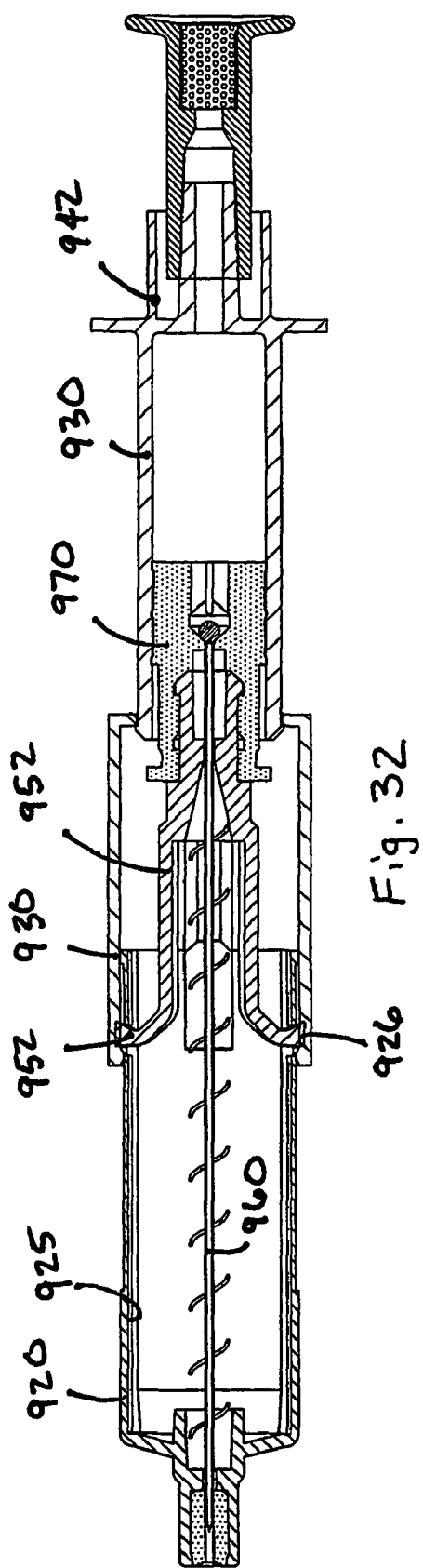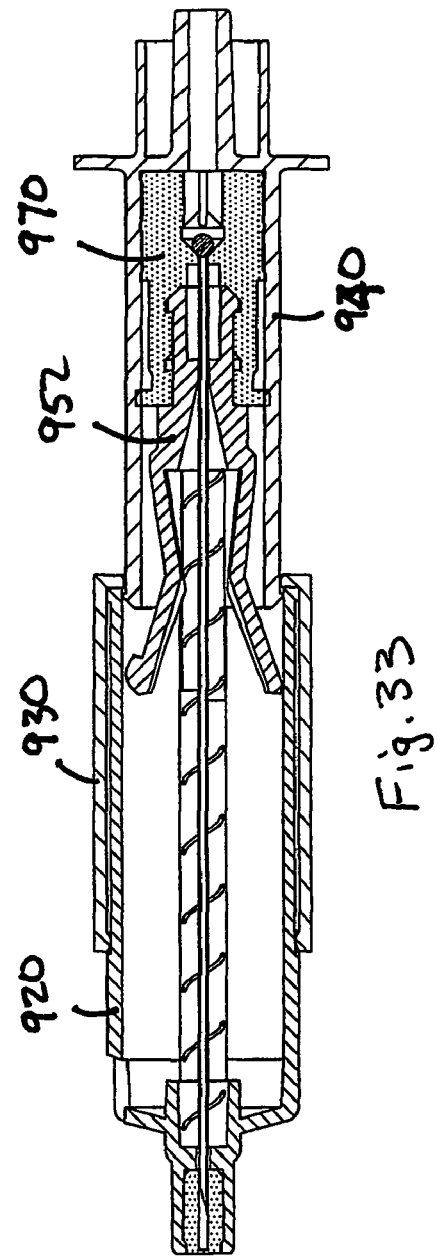

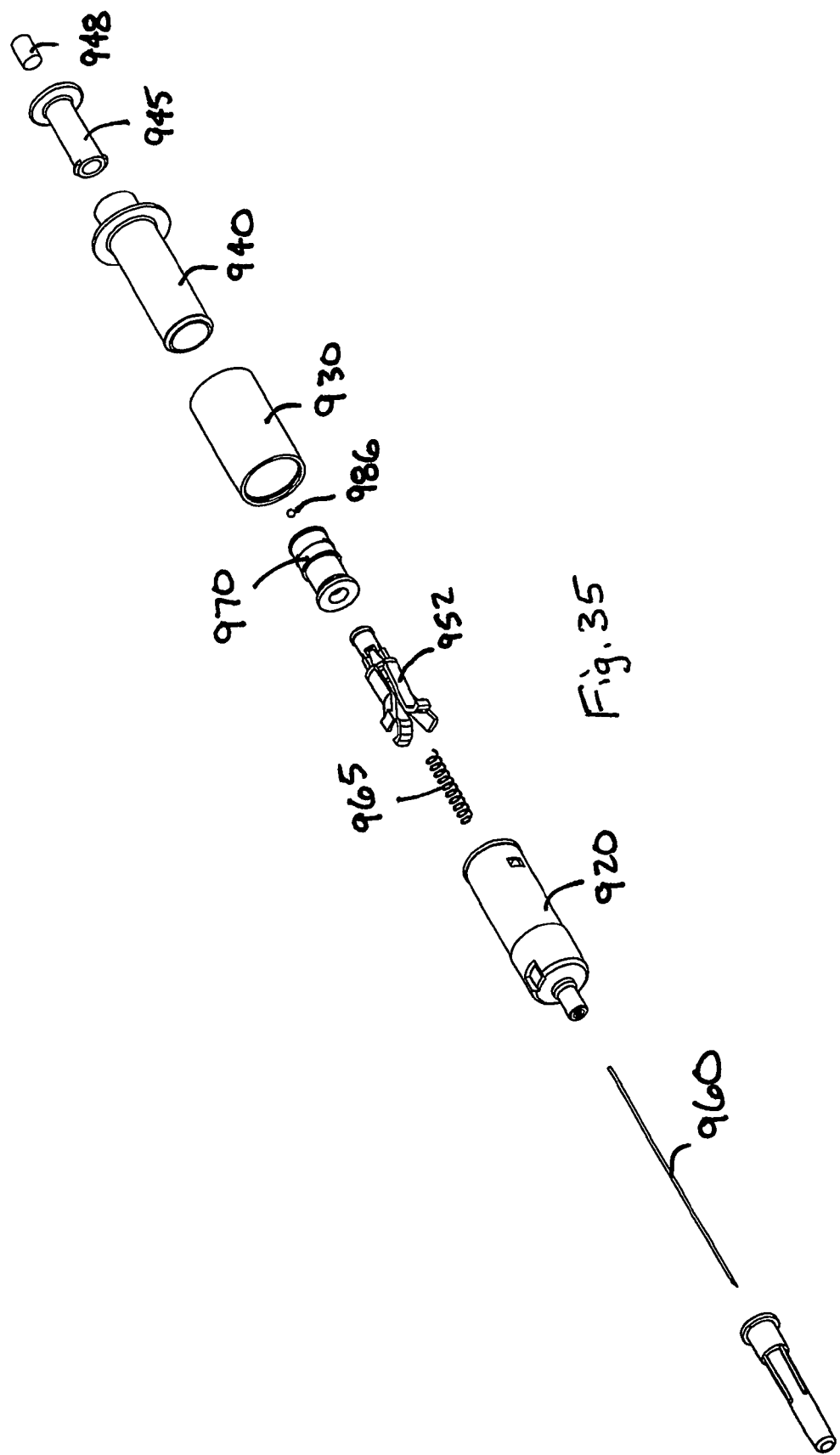

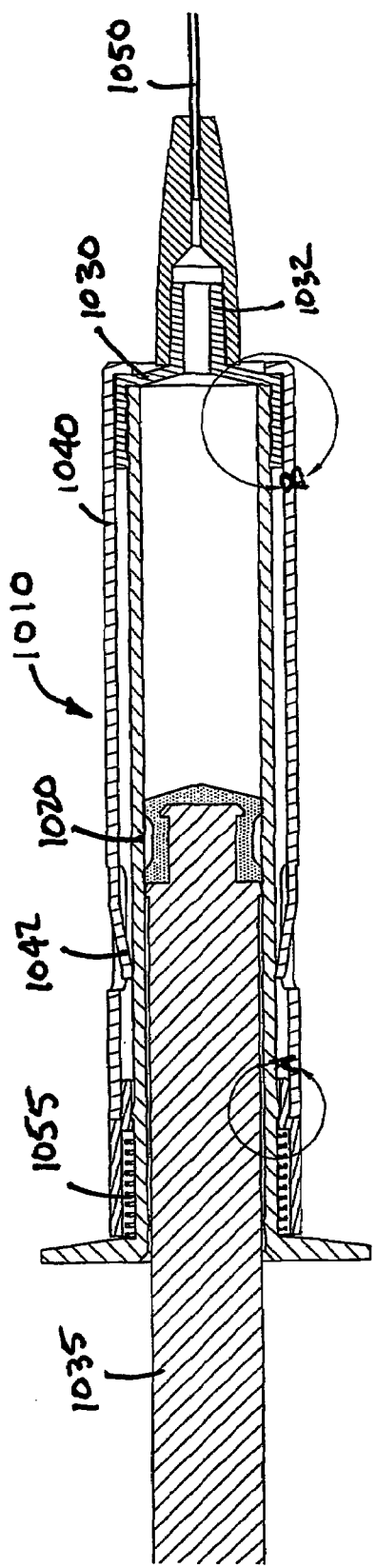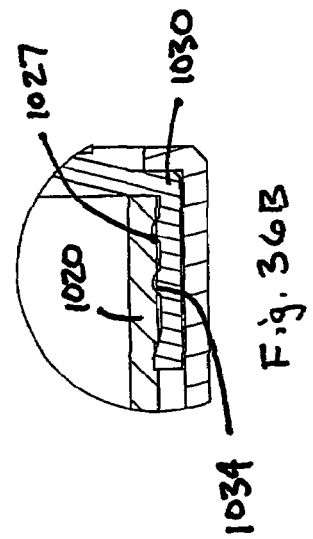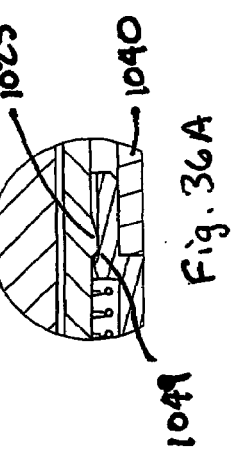
Fig. 36
Fig. 36A
Fig. 36B

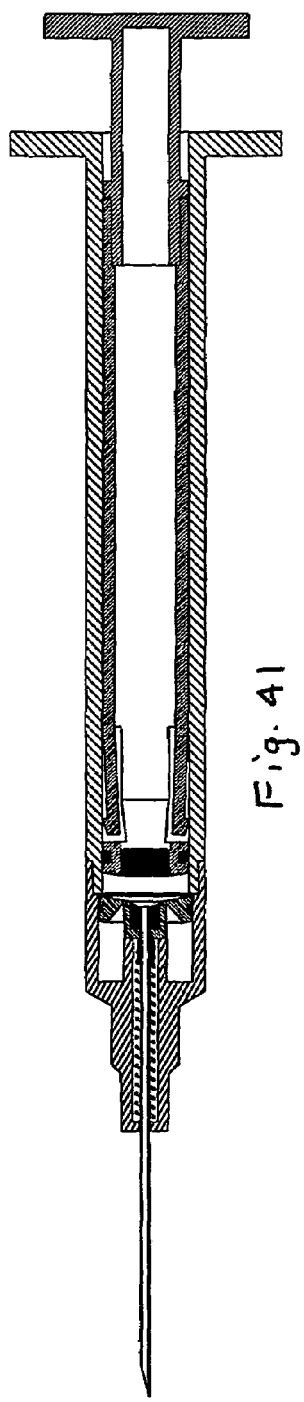
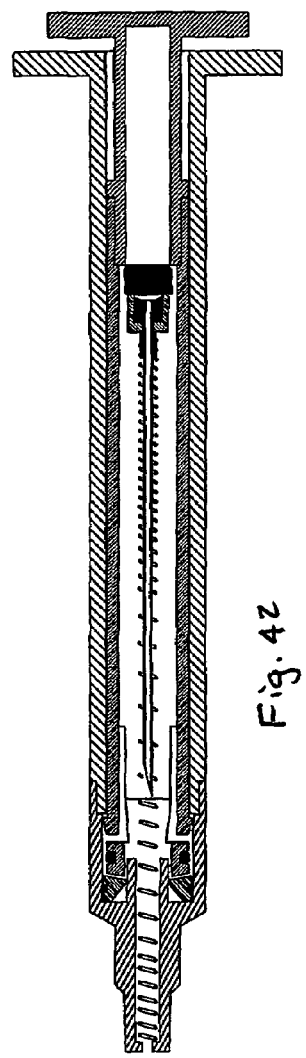
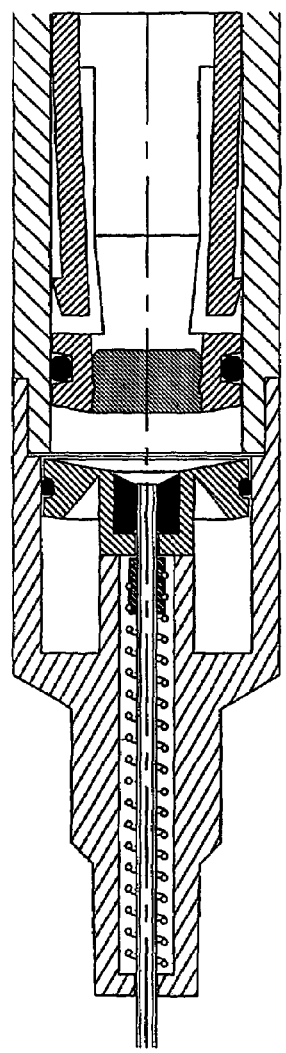
Fig. 41
Fig. 42
Fig. 43

SAFETY NEEDLE MEDICAL BEARING DEVICES

FIELD OF THE INVENTION

The present invention relates to syringes for administering injections of medicinal fluids to a patient or withdrawal of fluid, such as blood from a patient. More specifically, the invention relates to such devices having a retractable needle feature for rendering the device non-reusable and safely disposable. This application claims priority to U.S. Provisional Application No. 60/169,430 filed Dec. 7, 1999, which incorporate herein by reference.

BACKGROUND OF THE INVENTION

Various types of medical devices employ a needle for piercing the skin of a patient for diagnostic or therapeutic purposes. One such device is a hypodermic syringe. Handling of such needle-bearing medical devices after the needle is withdrawn from the patient can result in transmission of various pathogens, most notably human immune virus (HIV), to uninfected medical personnel, due to an inadvertent needle stick. Accordingly, it is desirable to provide a device for injecting medication or withdrawing fluid, wherein the needle is retracted into the housing of the device after use.

DESCRIPTION OF THE DRAWINGS

All of the objects of the present invention are more fully set forth hereinafter with reference to the accompanying drawings, wherein:

FIG. 1 is a cross-sectional view of a first needle-bearing medical device, in which the needle is retractable after use;

FIG. 2 is a cross-sectional view of the medical device illustrated in FIG. 1, in which medicine is aspirated into the device;

FIG. 3 is a cross-sectional view of the medical device illustrated in FIG. 1, illustrating the device just prior to retraction of the needle;

FIG. 4 is a cross-sectional view of the medical device illustrated in FIG. 1, illustrating the device after retraction;

FIG. 5 is a cross-sectional view of the medical device illustrated in FIG. 1, illustrating the device after retraction;

FIG. 6 is a cross-sectional view of a second needle-bearing medical device, in which the needle is retractable after use;

FIG. 7 is a cross-sectional view of the medical device illustrated in FIG. 6, illustrating the device after retraction;

FIG. 7A is an enlarged fragmentary view of the medical device illustrated in FIG. 7;

FIG. 8 is a partially broken away perspective view of the medical device illustrated in FIG. 6;

FIG. 8A is an enlarged fragmentary perspective view of the portion designated A of the medical devices illustrated in FIG. 8;

FIG. 8B is an enlarged fragmentary perspective view of the portion designated B of the medical devices illustrated in FIG. 8;

FIG. 9 is a partially broken away perspective view of the medical device illustrated in FIG. 6, illustrating the device after retraction;

FIG. 10 is a partially broken away exploded perspective view of the medical device illustrated in FIG. 6;

FIG. 11 is a cross-sectional view of a third needle-bearing medical device, in which a shield covers the needle after use;

FIG. 12 is a plan view of the medical device illustrated in FIG. 11;

FIG. 13 is a perspective view of the medical device illustrated in FIG. 11;

FIG. 14 is a cross-sectional view of the medical device illustrated in FIG. 11, illustrating the device just prior to advancement of the shield;

FIG. 15 is a cross-sectional view of the medical device illustrated in FIG. 11, illustrating the device after the shield is advanced;

FIG. 16 is a cross-sectional view of a fourth needle-bearing medical device, in which a shield covers the needle after use;

FIG. 17 is a cross-sectional view of the medical device illustrated in FIG. 16, illustrating the device just prior to advancement of the shield;

FIG. 18 is a cross-sectional view of the medical device illustrated in FIG. 16, illustrating the device after the shield is advanced;

FIG. 21 is a cross-sectional view of a fifth needle-bearing medical device, in which the needle is retractable after use;

FIG. 22 is a cross-sectional view of the medical device illustrated in FIG. 21, illustrating the device after retraction;

FIG. 28 is a cross-sectional view of the medical device illustrated in FIG. 26, illustrating the device after retraction;

FIG. 29 is a cross-sectional view of a ninth needle-bearing medical device, in which the needle is retractable after use;

FIG. 30 is a cross-sectional view of the medical device illustrated in FIG. 29;

FIG. 32 is a cross-sectional view of the medical device illustrated in FIG. 29, illustrating the device after retraction;

FIG. 33 is a cross-sectional view of the medical device illustrated in FIG. 30, illustrating the device after the fluid specimen has been expelled;

FIG. 35 is an exploded perspective view of the device illustrated in FIG. 30;

FIG. 36 is a fragmentary cross-sectional view of a tenth needle-bearing medical device, in which a shield covers the needle after use;

FIG. 36A is an enlarged fragmentary cross-sectional view of the portion designated A of the medical device illustrated in FIG. 36;

FIG. 36B is an enlarged fragmentary cross-sectional view of the portion designated B of the medical device illustrated in FIG. 36;

FIG. 41 is a cross-sectional view of an eleventh needle-bearing medical device, it which the needle is retractable after use;

FIG. 42 is a cross-sectional view of the medical device illustrated in FIG. 41, illustrating the device after retraction; and FIG. 43 is an enlarged fragmentary cross-sectional view of the medical device illustrated in FIG. 41.

DETAILED DESCRIPTION OF THE PREFERRED EMBODIMENTS

First Device

Figure 19:
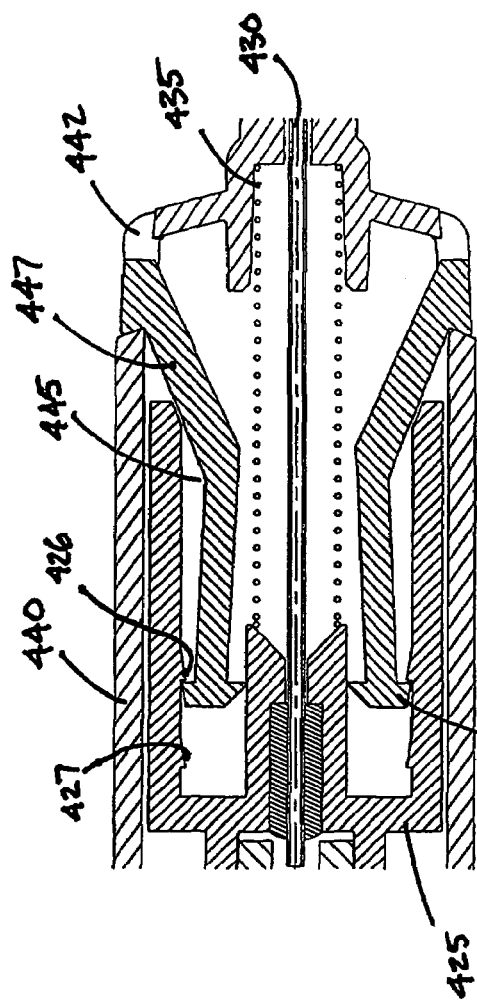
FIG. 19 is an enlarged fragmentary cross-sectional view of the medical device illustrated in FIG. 16.
Figure 20:
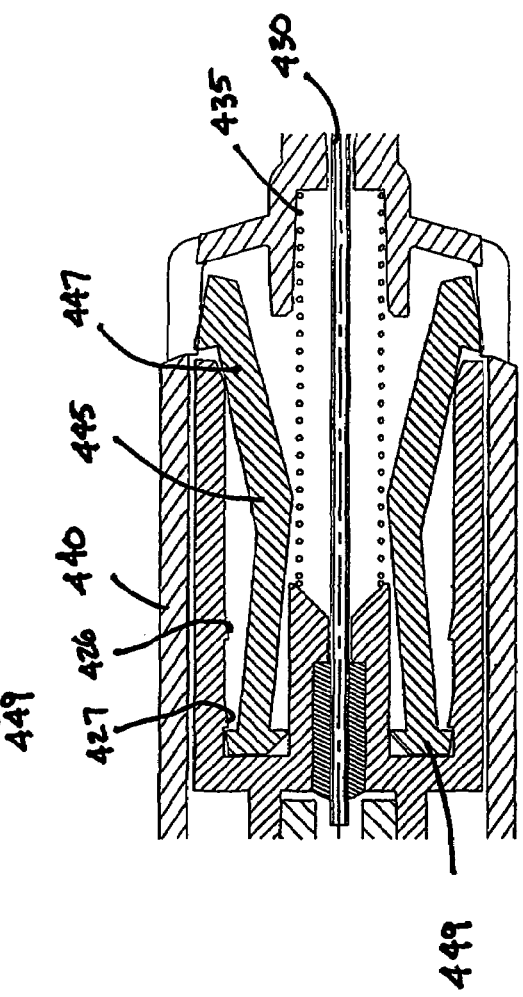
FIG. 20 is an enlarged fragmentary cross-sectional view of the medical device illustrated in FIG. 17.

Referring now to FIGS. 1-5, a syringe 10 having a retractable needle 60 is illustrated. The syringe includes a needle retainer 40 for releasably retaining the needle during use. A plunger 35 is operable to aspirate medicine into the syringe and expel medicine from the syringe into a patient. At the end of an injection stroke, the plunger 35 engages the needle retainer 40 to release the needle for retraction. A spring 55 then displaces the needle 60 rearwardly so that the contaminated needle is shielded within the syringe 10.

The syringe 10 includes a generally cylindrical hollow barrel 20. The rearward end of the barrel is open for receiving the plunger 35. The forward end of the barrel is generally closed, having a reduced diameter opening through which the needle 60 projects. A pair of retaining holes 22 are formed in the side of the barrel adjacent the forward end of the barrel. The retaining holes 22 cooperate with the needle retainer 40 to retain the needle 60 prior to retraction. A pair of lockout openings 24 are formed in the side of the barrel adjacent the rearward end of the barrel (see FIG. 5). The lockout openings 24 cooperate with a pair of locking arms 50 to lock the needle in a retracted position.

An axially elongated stem 30 is disposed within the barrel 20. The stem cooperates with the plunger 35 to effectuate aspiration and expulsion of medicine into and out of the syringe. Specifically, the stem 30 includes a seal 32 disposed at the rearward end of the stem. The needle 60 is fixedly attached to the stem 30 by an adhesive, such as epoxy, so that the forward sharpened tip of the needle projects forwardly from the stem, and the rearward end of the needle projects into an opening at the rearward end of the stem, adjacent the seal 32. The stem is generally hollow, and a spring disk 34 is attached to the stem within the hollow portion of the stem. The spring disk 34 provides bearing surface against which the rearward end of the spring 55 bears.

The plunger 35 is an axially elongated generally hollow cylinder having an open forward end and a closed rearward end. The interior of the plunger 35 forms a cavity 37 for receiving medicinal fluid. The diameter of the cavity 37 is sized to cooperate with the exterior diameter of the seal 32 on the stem 30 to provide a fluid tight seal between the plunger and the stem. The forward end of the plunger 35 forms a rim for engaging the needle retainer 40 as described further below. A thumb pad 39 is formed at the rearward end of the plunger 35 to facilitate manual operation of the plunger. Specifically, the thumb pad 39 forms a surface that the user can press against to advance the plunger to expel fluid from the syringe.

The needle 60 is operable between an extended position in which the sharpened tip of the needle is exposed for use and a retracted position in which the sharpened tip is shielded within the barrel to prevent inadvertent contact with the sharpened tip. The spring 55 circumscribes the needle 60, and biases the needle and attached stem 30 rearwardly toward the retracted position. The needle retainer 40 releasably retains the needle and attached stem in the extended position.

The needle retainer 40 comprises at least one and preferably two radially deformable arms 42. The ends of the arms 42 form latches that engage the retaining holes 22 in the barrel to retain the needle against the bias of the spring 55. The needle retainer arms 42 are connected to the stem 30, and preferably are integrally formed with the stem. At least a portion of the needle retainer arms 42 extend transverse the central axis of the barrel 20. This transverse portion of each needle retainer arm forms an engagement surface that cooperates with the forward rim of the plunger 35, as discussed further below.

Configured in this way, the device operates as follows. FIG. 1 illustrates the syringe 10 as it is shipped. A needle cover 15 encloses the forward end of the needle 60 to maintain the sterility of the needle. Referring to FIG. 2, the needle cover 15 is removed, and medication can be aspirated into the syringe from a vial by inserting the sharpened tip into the vial and displacing the plunger 35 rearwardly. The fluid tight seal between the seal 32 and the interior of the plunger 35 create a vacuum as the plunger is displaced rearwardly. In response, fluid flows from the vial through the needle and into the plunger cavity 37 that is in fluid communication with the needle. This procedure for aspirating the syringe 10 is essentially the same as the procedure for aspirating a typical non-safety syringe. However in the present instance, the medicine is aspirated into the plunger 35, rather than into the barrel 20, as occurs in a typical non-safety syringe.

After medicine is aspirated into the syringe, the medicine can be injected into a patient by pressing against the thumb pad 39 to displace the plunger 35 forwardly. The medicine flows from the plunger cavity 37 through the needle 60 and into the patient. The distance from the rearward end of the seal 32 to the actuation surface of the needle retainer 40 is the same as the distance from the rim of the plunger to the end wall of the cavity 37 in the plunger. In this way, at the end of the injection stroke (i.e. substantially all of the medication is expelled from the plunger cavity 37), the rim of the plunger 35 engages the needle retainer arms 42, displacing the arms radially inwardly so that the arms disengage the retaining holes 22 in the barrel 20, as shown in FIG. 3.

Referring to FIG. 4, after the needle retainer 40 is released, the spring 55 displaces the stem 30 rearwardly. Since the needle 60 is attached to the stem 30, the needle is displaced rearwardly along with the stem. Further, since the plunger is in engagement with the stem 30, the plunger is also displaced rearwardly along with the stem.

Referring now to FIG. 5, a cross-sectional view that is taken through a plane orthogonal to the view in FIG. 4. This view shows the details of the locking feature of the syringe 10. Specifically, at least one, and preferably two radially deformable locking arms 50 project radially outwardly from the stem 30. The distance between the rearward end of the seal 32 and the locking arms 50 is greater than the distance from the forward rim of the plunger to the rearward wall of the plunger cavity 37, so that at the end of the injection stroke the plunger does not engage the locking arms.

When the stem 30 is disposed in the forward position, the locking arms 50 are displaced radially inwardly relative to the position illustrated in FIG. 5, and are in engagement with alignment grooves 26 formed in the interior of the barrel. The alignment grooves 26 are axially extending grooves that are substantially parallel to the axis of the barrel. As the stem 30 and needle 60 are retracted from the extended position, the locking arms 50 engage the alignment grooves 26 to guide the retraction of the stem and needle. The grooves and locking arms prevent the locking arms from rotating relative to the barrel. The alignment grooves intersect the lockout openings 24, so that at the end of retraction, the locking arms before radially outwardly into engagement with the lockout openings 24.

Second Device

Referring now to FIGS. 6-10, a second safety medical device is illustrated. The device 110 is a syringe having a retractable needle 160, so that after use the contaminated needle is protected against inadvertent contact.

The syringe 110 includes a cylindrical barrel 120 having a generally open forward end and a generally open rearward end. The forward end of the barrel 120 forms a socket 122 for receiving a slotted collar 130 that releasably retains a needle carrier 140. A plunger 150 is axially displaceable within the barrel. At the end of an injection stroke, the plunger 150 engages the needle carrier 140 to automatically actuate retraction of the needle 160.

The needle 160 has a sharpened tip that is operable between an extended position and a retracted position. In the extended position, the needle projects forwardly from the barrel 120 to facilitate an injection of medication. In the retracted position, the sharpened tip of the needle is enclosed within the barrel 120 to prevent inadvertent contact with the contaminated sharpened tip of the needle. A spring 155 biases the needle 160 toward the retracted position.

As showed in FIG. 10, preferably the needle 160 is bonded to a needle hub 162, forming a needle assembly similar to standard needle assemblies that are presently used in the medical profession. The needle hub has a connector, such as a Luer connector for attaching the needle assembly to the needle carrier 140.

The needle carrier 140 is adapted to engage the needle assembly and releasably retain the needle assembly against the bias of the spring 155. The needle carrier 140 includes A connector 146 such as a Luer connector that is configured to cooperate with the needle hub 162 to provide a fluid tight seal between the needle hub and the needle carrier. The needle carrier further includes a pin 142 that cooperates with the slotted collar 130 to releasably retain the needle 160 in the extended position, as discussed in greater detail below. In addition, preferably the needle carrier comprises a second pin circumferentially spaced from the pin 142 shown in FIG. 10, whereby the two pins are symmetrically disposed about the circumference of the needle carrier, and both pins cooperate with the collar 130.

A sealing ring 145 is attached to the rearward end of the needle carrier 140 to provide a fluid tight seal between the needle carrier and the barrel 120. The sealing ring 145 prevents fluid from leaking out the forward end of the barrel 120. In this way, the sealing ring 145 forms the forward wall for the fluid cavity within the barrel in which the medication is contained.

The needle carrier 140 is a generally cylindrical element having a through bore that operates as a fluid passage between the interior of the barrel and the needle. In this way, when a needle assembly 160,162 is attached to the needle carrier, the needle is in fluid communication with the fluid cavity within the barrel.

The spring 155 is disposed between the slotted collar 130 and the needle carrier 140 biasing the needle carrier rearwardly. The spring 155 circumscribes the needle carrier 140, and the rearward end of the spring engages a circumferential flange projecting radially outwardly from the rearward end of the needle carrier adjacent the sealing ring 145.

Referring to FIGS. 8A and 8B, the details of the slotted collar 130 are illustrated in greater detail. As shown in FIG. 8A, the slotted collar 130 is a generally cylindrical collar engaged with the socket 122 at the forward end of the barrel 120 to fixedly attach the collar to the barrel. Specifically, the socket 122 comprises an annular ridge 123 at the forward end of the barrel and an annular flange 124 axially spaced from the forward ridge. The ridge 123 and flange 124 operate to retain the collar within the socket 122. In addition, preferably, the slotted collar 130 comprises in alignment key 131 that aligns the slotted collar at a predetermined circumferential position relative to the barrel 120. The alignment key 131 cooperates with an axial groove formed in the socket 122 of the barrel. Although the connection between the slotted collar 130 and barrel has been described above as a snap fit or press it engagement, the slotted collar can be fixedly attach to the barrel in a number of other ways. For instance, the slotted collar can be bonded to the barrel 120, such as by epoxy.

The slotted collar 130 comprises at least one, and preferably two pin slots 132 that cooperate with retaining pins 142 attached to the needle carrier 140. The pin slots 132 are disposed transverse the axis of the syringe. Referring to FIGS. 8A and 8B, an axial groove 134 intersects the pin slots 132. The rearward edge of the pin slot 132 forms a shoulder that engages the pin 142 to retain the needle carrier, as shown in FIG. 8B. The depth of the axial groove 134 is greater than the length of the pin 142 that projects into the pin slot 132. Therefore, when the needle carrier 140 is twisted so that the pin 142 is circumferentially aligned with the axial groove 134, the needle carrier 140 is free to move axially rearwardly relative to the collar 130.

Accordingly, the syringe 110 operates as follows. Prior to use the user selects a needle assembly and attaches it to the needle carrier 140. A dose of medication is then aspirated into the syringe by displacing the plunger rearwardly. The plunger 150 includes a piston 152 that forms a fluid-tight seal with the interior wall of the barrel. Therefore, displacing the plunger rearwardly forms a vacuum within the barrel, so that medicine is drawn into the barrel with the plunger is displaced rearwardly.

At the end of the injection stroke, the plunger 150 engages the needle carrier 140. Continued forward axial displacement of the plunger 150 drives the needle carrier 140 forwardly. The engagement between the pins 142 and the angled pin slots 132 operate like a cam and follower, causing the needle carrier to rotate until the pins are aligned with the axial grooves 134. The spring 155 then drives the needle carrier 140 and attached needle 160 rearwardly into the retracted position. In addition, since the plunger 150 is engaged with the needle carrier 140, the plunger 150 is also displaced rearwardly as the needle is retracted. Preferably, the barrel includes a locking rib 126 projecting radially inwardly from the interior wall of the barrel, adjacent the rearward end of the barrel. The locking rib 126 engages the plunger, acting as a stop to impede continued rearward displacement of the plunger. In this way, the locking rib 126 prevents the plunger, needle carrier 140 and needle 160 from being displaced out the rearward end of the barrel by the spring.

Third Device

Referring now to FIGS. 11-15, a third device 310 is illustrated. The device 310 is a syringe having a shield 330 for covering a needle 360 after use. The syringe includes a barrel 320 and a plunger 340 that are similar to commonly used non-safety syringes. However, the barrel 320 and plunger 340 are configured so that at the end of the injection stroke continued axial force on the plunger releases the shield 330, and a spring 355 displaces the shield 330 forwardly over the used needle 360 to shield the contaminated needle against inadvertent contact.

The barrel 320 is a generally hollow cylinder having a generally closed forward end with a reduced diameter opening forming a fluid passage, and a rearward end that is substantially open for receiving the plunger 340. The plunger 340 includes a piston 344 in fluid-tight engagement with the interior wall of the barrel for aspirating medicine into the syringe and injecting medicine into a patient from the syringe. A connector 322 is formed on the forward end of the barrel 320, and is configured to attach the needle 360 to the barrel. Preferably, the connector 322 is a threaded Luer connector.

The needle 360 is fixedly attached to a needle hub 362 to form a needle assembly similar to those commonly used with non-safety medical devices. Specifically, the needle hub 362 is adapted to cooperate with the connector 322 to attach the needle assembly to the barrel 320. Preferably, the needle hub comprises a female Luer connector providing a fluid tight seal between the needle assembly and the barrel. In this way, the needle assembly is readily attachable to the barrel by the user so that the needle is in fluid communication with the interior of the barrel.

The barrel 320 includes a shield lock 324 adjacent the connector 322. The shield lock 324 is a circumferential flange that operates to retain the shield 330 in an extended position after use. The shield lock 324 can be integrally formed with the barrel 320, however in the present instance, the shield lock 324 is formed on the outer surface of a collar disposed around the Luer connector 322. A flange 326 projects radially outwardly from the outer surface of the barrel 320 adjacent the rearward end of the barrel.

The shield 330 is a generally cylindrical sleeve overlying the barrel 320, so that the shield and barrel are preferably coaxial. The shield is operable between two positions, a retracted position and an extended position. In the retracted position, the needle 360 is exposed for use. In the extended position, the shield encloses the sharpened tip of the needle to prevent inadvertent needlesticks. A spring 355 disposed between the barrel and the shield biases the shield towards the extended position. Specifically, the spring is disposed between the flange 326 at the rearward end of the barrel, and an annular flange 334 projecting radially inwardly from the interior of the shield 330, as shown in FIG. 11.

At least one, and preferably two, shield latches 332 attached to the rearward end of the shield 330 releasably retain the shield in the retracted position. The shield latches 332 are radially deformable arms that engage the circumferential flange 326 formed at the rearward end of the barrel 320. The latches 332 have rearward facing actuations surfaces that are angled transverse the axis of the syringe. The actuations surfaces cooperate with a button cap 345 on the plunger 340 to release the shield 330, as discussed further below.

The plunger 340 is axially displaceable within the barrel. A piston 344 attached to the forward end of the plunger forms a fluid tight seal with the interior surface of the barrel. The rearward end of the plunger 340 comprises a thumb pad 342 projecting radially outwardly. The button cap 345 is attached to the thumb pad 342.

The button 345 is a generally cylindrical cup-shaped element having an interior diameter that corresponds to the diameter of the thumb pad 342. The button cap is operable between a first position and a second position. A detent 347 projects radially inwardly from the inner surface of the button cap to impede displacement of the button cap from the first position to the second position. The detent 347 cooperates with the thumb pad 342 to provide sufficient retention force to prevent the button cap from being displaced into the second position in response to forward axial force applied to the button cap to displace the plunger forwardly during an injection stroke.

Referring to FIG. 12, the syringe is illustrated in a position in which the plunger is completely inserted into the barrel so that the piston 344 engages the front wall of the barrel. This is the position of the plunger at the end of an injection stroke. In FIG. 11, the button cap 345 is shown in its first position. In this position, the forward rim of the button cap does not engage the shield latches 332. At the end of the injection stroke, the button cap 345 can be displaced into the second position by applying sufficient forward axial force to the button cap to overcome the retention forced provided by the engagement between the detent 347 and the thumb pad 342.

Referring to FIG. 14, as the button cap 345 is displaced into the second position, the forward rim of the button cap engages the actuations surfaces of the shield latches 332 deforming the shield latches radially outwardly out of engagement with the flange 326. The spring 355 then displaces the shield 330 forwardly into the extended position to cover the needle 160. The shield includes a shield retainer 335 in the form of a pair of radially deformable latches formed in the side wall of the shield, as shown in FIG. 13. As the shield 330 is displaced forwardly, the shield retainer engages the shield lock 324 at the forward end of the barrel 320 to lock the shield in the extended position, thereby preventing re-exposure of the needle 160.

Referring now to FIGS. 16-20, a fourth safety medical device is illustrated. The device is a combination safety needle assembly 420 and syringe 410. The syringe 410 is the same as commonly used non-safety hypodermic syringes. The needle assembly 420 is adapted to cooperate with the syringes 410 that are presently available so that they can be used with a safe needle assembly without modification. Specifically, the needle assembly 420 includes a needle 430 having a sharpened tip and a shield 440 that extends over the needle after use to prevent inadvertent contact with the contaminated needle.

The syringe 410 includes a hollow cylindrical barrel 415 and a plunger 417 reciprocally displaceable within the barrel to infuse medicine into the barrel or expel fluid out of the barrel. The forward end of the barrel 415 comprises a connector 419 such as a Luer connector for attaching the needle assembly to the barrel prior to use. In the present instance, the plunger 417 is illustrated as a standard plunger used in connection with hypodermic syringes, in which the plunger comprises an axially elongated plunger rod and a piston attach to the forward end of the plunger rod. However, it may be desirable to use the needle assembly 420 with syringes that are used for drawing blood specimens and inserting guide wires. Specifically, the plunger may include a bore for receiving a guide wire, along with a valve for preventing fluid from leaking into the bore from the syringe. During use, a guide wire is inserted through the plunger and is fed through the needle 430 into a patient.

The needle assembly 420 includes a needle hub 425 for attaching the needle assembly 420 to the barrel 415. The needle hub 425 includes a connector, such as a Luer connector that cooperates with the connector 419 of the barrel to form a fluid-tight seal between the needle assembly and the syringe. The needle 430 is fixedly attached to the needle hub 425.

The 440 is operable between a retracted position, in which the needle is exposed for use as shown in FIG. 17, and an extended position in which the shield covers the sharpened tip of the needle as shown in FIG. 18. A spring 435 biases the shield 440 toward the extended position. A shield retainer 445 releasably retains the shield 440 in the retracted position against the bias of the spring 435.

The shield retainer 445 comprises at least one, and preferably two, radially deformable arms 447. The arms 447 comprise an actuation portion disposed transverse the central axis of the syringe. The forward ends of the arms form latches that cooperate with retainer openings 442 formed in the forward end of the shield 440. The ends of the arms 447 form a radially projecting flange 440 that cooperate with first and second locking ridges 426, 427 formed on the needle hub 425. Specifically, the first and second locking ridges 426, 427 are formed in the inner surface of the needle hub 425 projecting radially inwardly.

The locking ridges 426, 427 have a tapered forward edge and a perpendicular rearward edge, so that the locking ridges operate as one-way locks allowing the locking flange 449 of the retainer arms 447 to be displaced rearwardly relative to the needle hub, but not forwardly. In this way, the locking ridges 426, 427 cooperate with the locking flange 449 to retain the retainer arms 447 in first and second axial positions.

The forward edge of the needle hub 425 forms a rim configured to cooperate with the actuation portion of the retaining arms 447. During use of the device, the shield retainer 445 is disposed so that the locking flange 449 engages the first locking ridges 446 as shown in FIGS. 16 and 19. Referring to FIGS. 17 and 19, after use, pulling the shield rearwardly displaces the shield retainer 445 rearwardly relative to the needle hub 425. This displaces the locking flange 449 into engagement with the second locking ridges 427 thereby substantially permanently locking shield retainer 445 in a rearward position. In addition, pulling the shield rearwardly after use displaces the retaining arms 447 into engagement with the forward rim of the needle hub 425, so that the needle hub displaces the arms radially inwardly out of engagement with the openings 442 in the shield. The spring 435 then displaces the shield 440 forwardly into the extended position to cover the needle as shown in FIG. 18.

Fourth Device

Referring now to FIGS. 16-20, a fourth safety medical device is illustrated. The device is a combination safety needle assembly 420 and syringe 410. The syringe 410 is the same as commonly used non-safety hypodermic syringes. The needle assembly 420 is adapted to cooperate with the syringes 410 that are presently available so that they can be used with a safe needle assembly without modification. Specifically, the needle assembly 420 includes a needle 430 having a sharpened tip and a shield 440 that extends over the needle after use to prevent inadvertent contact with the contaminated needle.

The syringe 410 includes a hollow cylindrical barrel 415 and a plunger 417 reciprocally displaceable within the barrel to infuse medicine into the barrel or expel fluid out of the barrel. The forward end of the barrel 415 comprises a connector 419 such as a Luer connector for attaching the needle assembly to the barrel prior to use. In the present instance, the plunger 417 is illustrated as a standard plunger used in connection with hypodermic syringes, in which the plunger comprises an axially elongated plunger rod and a piston attach to the forward end of the plunger rod. However, it may be desirable to use the needle assembly 420 with syringes that are used for drawing blood specimens and inserting guide wires. Specifically, the plunger may include a bore for receiving a guide wire, along with a valve for preventing fluid from leaking into the bore from the syringe. During use, a guide wire is inserted through the plunger and is fed through the needle 430 into a patient.

The needle assembly 420 includes a needle hub 425 for attaching the needle assembly 420 to the barrel 415. The needle hub 425 includes a connector, such as a Luer connector that cooperates with the connector 419 of the barrel to form a fluid-tight seal between the needle assembly and the syringe. The needle 430 is fixedly attached to the needle hub 425.

The 440 is operable between a retracted position, in which the needle is exposed for use as shown in FIG. 17, and an extended position in which the shield covers the sharpened tip of the needle as shown in FIG. 18. A spring 435 biases the shield 440 toward the extended position. A shield retainer 445 releasably retains the shield 440 in the retracted position against the bias of the spring 435.

The shield retainer 445 comprises at least one, and preferably two, radially deformable arms 447. The arms 447 comprise an actuation portion disposed transverse the central axis of the syringe. The forward ends of the arms form latches that cooperate with retainer openings 442 formed in the forward end of the shield 440. The ends of the arms 447 form a radially projecting flange 440 that cooperate with first and second locking ridges 426, 427 formed on the needle hub 425. Specifically, the first and second locking ridges 426, 427 are formed in the inner surface of the needle hub 425 projecting radially inwardly.

The locking ridges 426, 427 have a tapered forward edge and a perpendicular rearward edge, so that the locking ridges operate as one-way locks allowing the locking flange 449 of the retainer arms 447 to be displaced rearwardly relative to the needle hub, but not forwardly. In this way, the locking ridges 426, 427 cooperate with the locking flange 449 to retain the retainer arms 447 in first and second axial positions.

The forward edge of the needle hub 425 forms a rim configured to cooperate with the actuation portion of the retaining arms 447. During use of the device, the shield retainer 445 is disposed so that the locking flange 449 engages the first locking ridges 446 as shown in FIGS. 16 and 19. Referring to FIGS. 17 and 19, after use, pulling the shield rearwardly displaces the shield retainer 445 rearwardly relative to the needle hub 425. This displaces the locking flange 449 into engagement with the second locking ridges 427 thereby substantially permanently locking shield retainer 445 in a rearward position. In addition, pulling the shield rearwardly after use displaces the retaining arms 447 into engagement with the forward rim of the needle hub 425, so that the needle hub displaces the arms radially inwardly out of engagement with the openings 442 in the shield. The spring 435 then displaces the shield 440 forwardly into the extended position to cover the needle as shown in FIG. 18.

Fifth Device

Referring now to FIGS. 21-22, a fifth safety medical device is illustrated. The device is a needle assembly 510 that is operable in connection with a number of standard medical devices having a cooperating connector, such as the syringe 410 illustrated and described above. However, the needle assembly 510 is particularly suited for use in connection with a medical device for inserting a guidewire 515 into a patient.

The needle assembly 510 comprises a housing that is preferably formed of two pieces, namely a rear housing 520 and a forward housing 525. The needle assembly also includes a needle 445 that is operable between a projecting position in which the sharpened tip of the needle is exposed for use, and a retracted position in which the sharpened tip is protected against inadvertent contact. A spring 540 biases the needle rearwardly toward the retracted position, and a latch 435 releasably retains the needle in the extended position against the bias of the spring.

The spring 540 is bonded directly to the needle 545 along the length of the needle forward of the rearward end of the needle. Preferably the spring is bonded to the needle by epoxy. The rearward edge of the spring bears against the latch 535, thereby retaining the needle 545. A manually actuable pushbutton 537 is attached to the latch 535. The latch 535 has an opening that is larger than the diameter of the spring 540. Accordingly, depressing the pushbutton downwardly aligns the spring with the opening in the latch, thereby allowing the needle to retract rearwardly.

The forward end of the housing is generally closed having a reduced diameter opening through which the needle 545 extends. A nose seal 527 is disposed within the housing adjacent the forward opening, so that upon retraction, the nose seal seals the forward opening to prevent fluid from leaking out of the needle assembly.

A generally cylindrical needle chamber 530 is disposed within the housing extending between the rear housing 520 and the forward housing 525. The rearward end of the rear housing 520 is generally opened forming a connector such as a Luer fitting 522 for attaching the needle assembly 510 to a medical device. An end wall 524 adjacent the Luer fitting 522 has a reduced diameter opening through which fluid and/or a guidewire 515 can pass.

A valve 550 is attached to the rearward end of the needle 545. The valve operates to prevent residual fluid in the needle from spitting out the forward end of the needle as the needle is retracted. In addition, the valve 550 includes rearward facing tapered surfaces for aligning a guidewire with the opening at the back end of the needle to thread the guide wire through the needle.

Sixth Device

Figure 23:
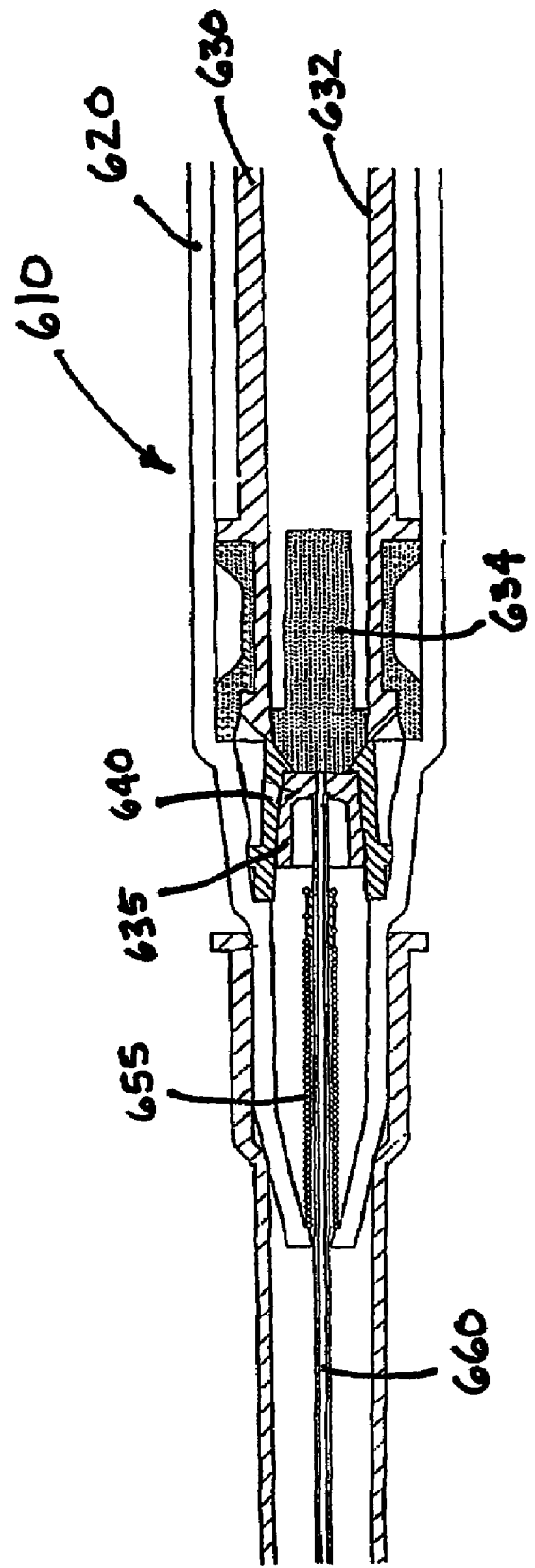
FIG. 23 is a fragmentary cross-sectional view of a sixth needle-bearing medical device, in which the needle is retractable after use.
Figure 24:
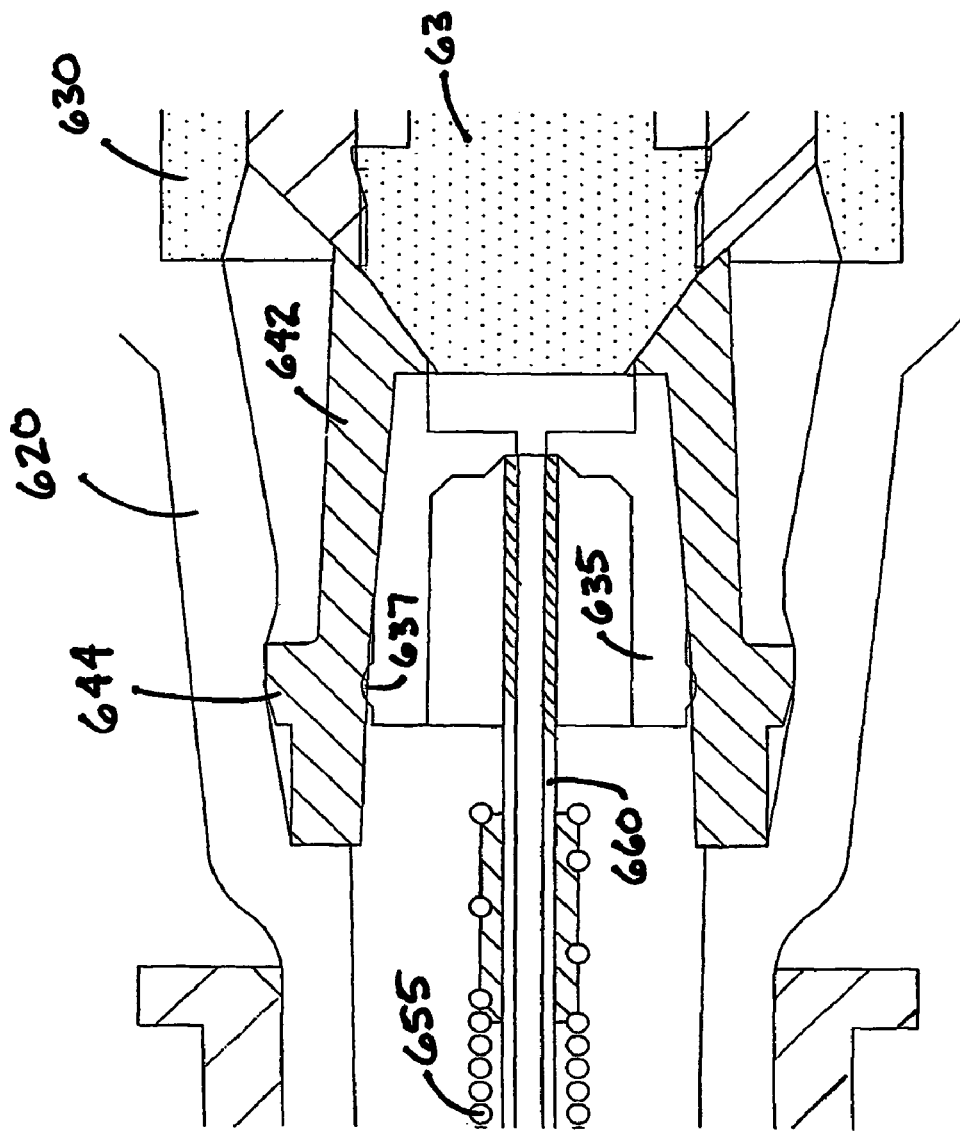
FIG. 24 is an enlarged fragmentary cross-sectional view of the medical device illustrated in FIG. 23.

Referring now to FIGS. 23 and 24, a sixth safety medical device is illustrated. The device is a hypodermic syringe 610 having a retractable needle 660. The syringe includes a needle retainer 640 releasably retaining the needle 660 in an extended position. A plunger 630 is configured to cooperate with the needle retainer to release the needle 660 after use.

The syringe 610 includes a hollow generally cylindrical barrel 620 having an open rearward end for receiving the plunger 630. The forward end of the barrel 620 tapers inwardly forming a nose. The plunger 630 is axially displaceable within the barrel, and forms a fluid-tight seal with the interior wall of the barrel.

The plunger is hollow, having a cavity 632 for receiving the needle 660 after it is retracted. The forward end of the plunger has an opening sized to receive the needle after it is retracted. A disassociable plunger 634 seals the opening at the forward end of the plunger to prevent fluid from entering the cavity 632 during aspiration of medicine into the barrel or expulsion of the medicine during an injection stroke. In the present instance, the plunger 634 frictionally engages the plunger. Alternatively, the plunger may be frangibly attached to the plunger. In either instance, the connection between the plunger and the plug is greater than the hydraulic pressure applied to the plug during an injection stroke.

The needle 660 has a sharpened tip for piercing a patient, and is operable between a projecting position in which the sharpened tip is exposed for use and a retracted position in which the needle is disposed within the plunger cavity 632 to protect the contaminated needle against inadvertent contact. A spring 655 bonded to the needle biases the needle toward the retracted position. The needle retainer 640 releasably retains the needle 660 against the bias of the spring.

The needle retainer comprises a bore. A needle seal 635 disposed within the bore of the needle retainer provides a fluid-tight seal between the seal and the needle retainer. The seal 635 is a cup shaped element having a substantially open forward end and a substantially closed rearward end. A fluid passageway extends through the closed rearward end of the seal 635. The spring 655 biases the needle 660 against the closed end of the seal 635 so that the needle abuts the fluid passageway, whereby the bore of the needle is aligned with the fluid passageway of the seal.

A circumferential rib 637 projects radially outwardly around the circumference of the seal 635 and into engagement with the bore of the needle retainer. The rib 637 provides a fluid-tight seal between the seal 635 and the bore of the needle retainer so that the fluid from the barrel does not leak out of the barrel between the needle retainer and the seal. In addition, the needle retainer 640 comprises a circumferential flange 644 forming a snap fit with a recess in the nose of the barrel formed to receive the needle retainer. The engagement between the flange 644 and the interior wall of the barrel forms a fluid-tight seal so that fluid does not leak from the barrel between the needle retainer and the wall of the barrel.

The needle retainer 640 comprises a plurality of axially elongated radially deformable fingers 642. The ends of the fingers form hooks or latches that engage the needle seal 635. Since the needle 660 abuts the needle seal 635, the needle retainer retains the needle along with the needle seal. The rearward surface of the fingers 642 taper radially outwardly, and the forward end of the plunger 630 is tapered to cooperate with the tapered surfaces of the fingers. In this way, at the end of an injection stroke, the tapered surfaces of the plunger 630 engage the tapered surfaces of the fingers 642, and operate like a wedge to deform the fingers radially outwardly out of engagement with the needle seal 635. As the plunger is displaced forwardly, the plug 634 at the end of the plunger engages the needle seal 635 and the needle seal dislodges the plug from the opening of the plunger, thereby providing access to the cavity. Accordingly, after the needle retainer releases the needle seal, the spring 655 propels the needle, needle seal, and plug rearwardly into the cavity of the plunger.

Seventh Device

Figure 25:
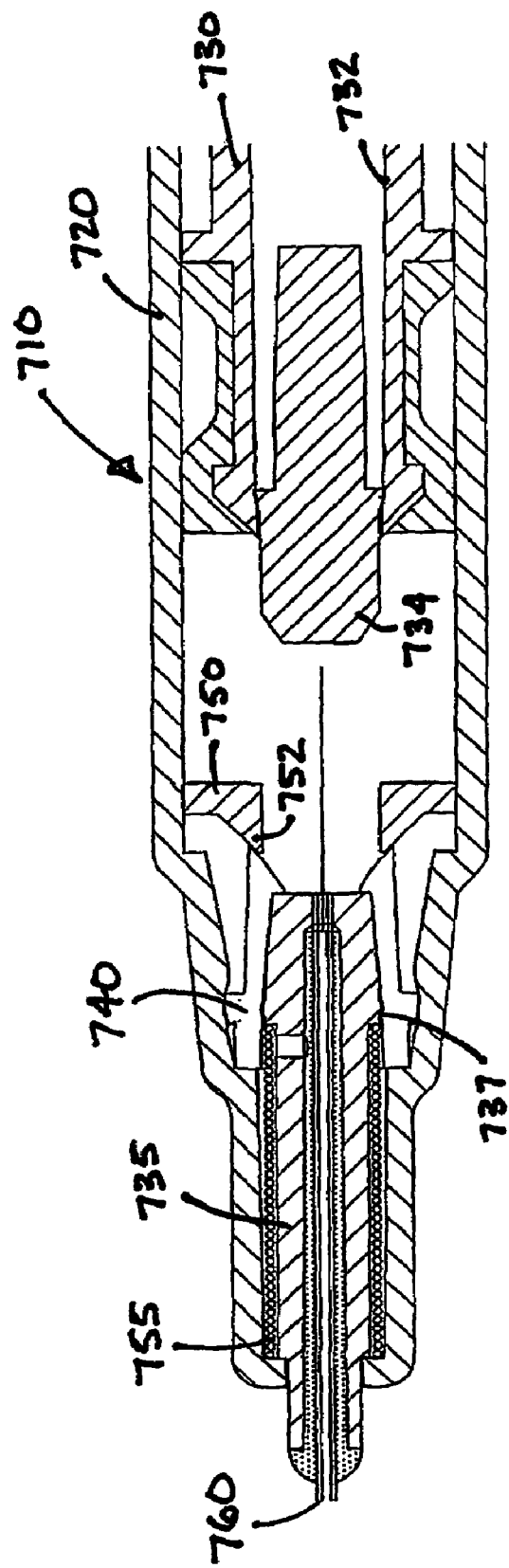
FIG. 25 is a fragmentary cross-sectional view of a seventh needle-bearing medical device, in which the needle is retractable after use.

Referring now to FIG. 25, a seventh safety medical device is illustrated. The device is a hypodermic syringe 710 having a retractable needle 760. The syringe 710 is similar to the syringe illustrated in FIGS. 23 and 24. Specifically, the syringe 710 has a barrel 720, plunger 730 and needle retainer 740 that are configured substantially similarly to the barrel 620, plunger 630 and needle retainer 640 of the syringe illustrated in FIGS. 23 and 24, and described above.

The syringe 710 in FIG. 25 differs from the syringe 610 in the following ways. The syringe 710 includes an axially elongated needle seal 735 having a bore for receiving the needle, and the needle is fixedly bonded to the needle seal within the bore. The needle seal includes a circumferential rib 737 forming a fluid-tight seal between the needle seal and the bore of the needle retainer 740, similar to the previous syringe 610.

The syringe 710 also comprises an actuator 750 disposed in the forward end of the barrel. The actuator 750 is a disk-like member having a tapered surface 752 projecting from its forward face. The tapered surface 752 is configured to cooperate with the needle retainer to deform the needle retainer fingers 742 radially outwardly to release the needle. The actuator is disposed between the forward end of the plunger 730 and the rearward end of the needle retainer 740. Accordingly, at the end of the injection stroke, the plunger engages the actuator 750 displacing the actuator axially forwardly so that the tapered surface 752 engages the needle retainer 740 to release the needle. In addition, the plug 734 sealing the opening to the cavity 732 of the plunger engages the needle seal 735, which dislodges the plug as the plunger is displaced forwardly. Therefore, after the needle is released by the needle retainer, the spring 755 displaces the needle rearwardly into the retracted position in the cavity of the plunger so that the sharpened tip of the needle is protected against inadvertent contact.

Eighth Device

Figure 26:
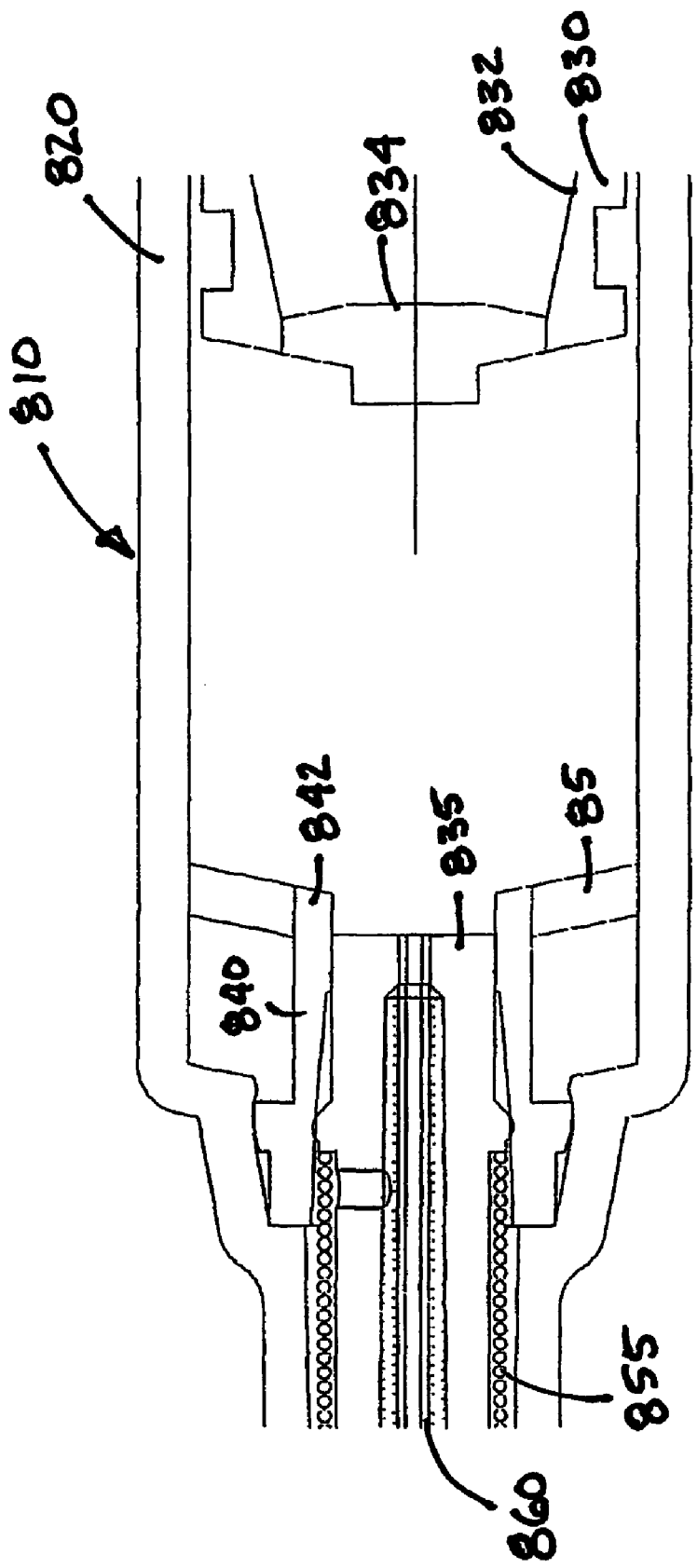
FIG. 26 is a fragmentary cross-sectional view of an eighth needle-bearing medical device, in which the needle is retractable after use.
Figure 27:
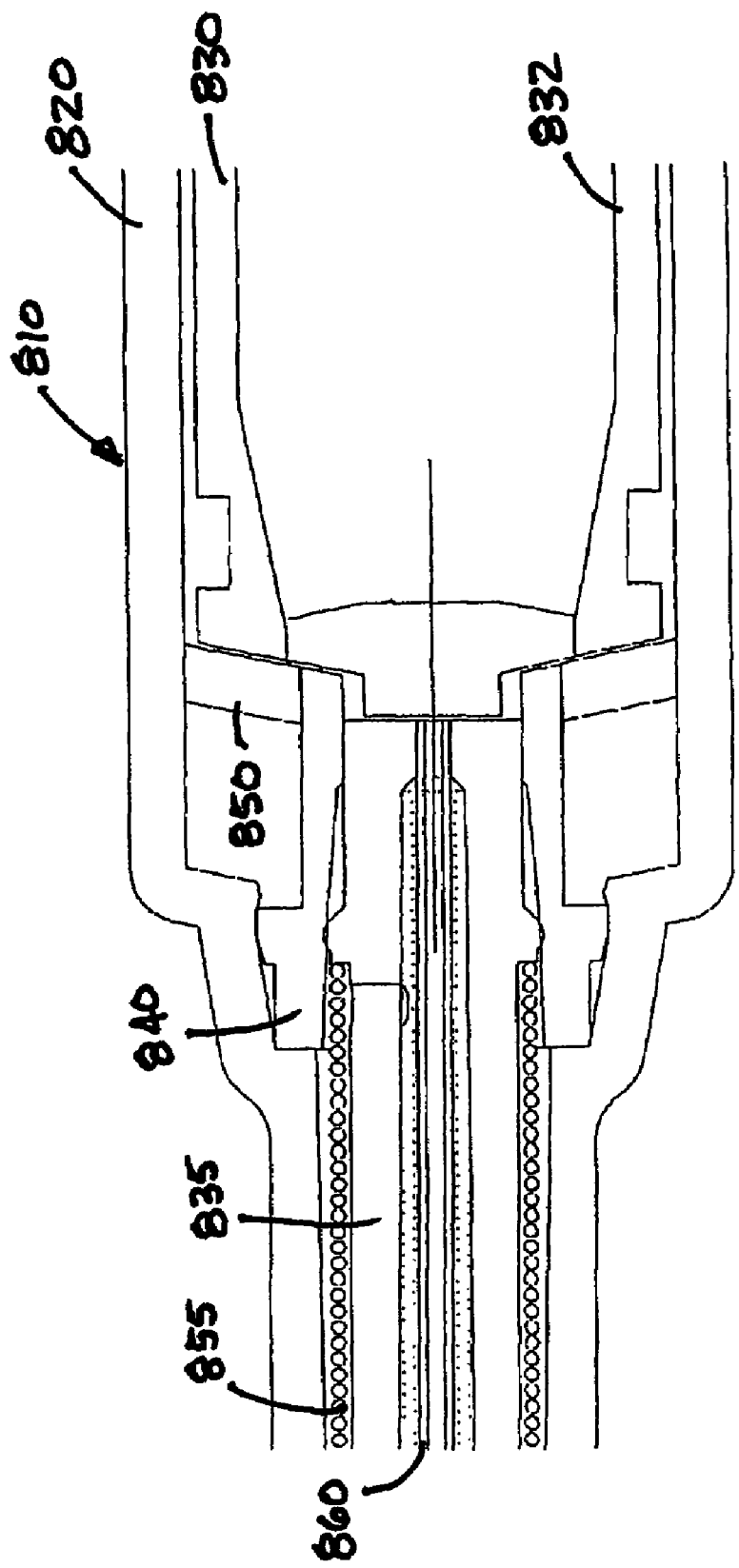
FIG. 27 is a cross-sectional view of the medical device illustrated in FIG. 26, illustrating the device just prior to retraction.

Referring now to FIGS. 26-28, an eighth safety medical device is illustrated. The device is a hypodermic syringe 810 having a retractable needle 860. The syringe is similar to the syringe illustrated in FIG. 25. Specifically, the syringe 810 has a barrel 820, plunger 830 and needle seal 835 that are configured substantially similarly to the barrel 720, plunger 730 and needle seal 735 of the syringe illustrated in FIG. 25, and described above.

The syringe 810 in FIGS. 26-28 differs from the syringe 710 in the following ways. The syringe 810 includes a collet-type needle retainer 840 and a retaining collar 850 that cooperates with the needle retainer. Specifically, the needle retainer comprises a plurality of axially elongated fingers 842 having engagement surfaces that engage the side of the needle seal 835. The fingers 842 are biased radially outwardly away from the needle seal 835. The retaining collar 850 retains the fingers 842 inwardly into engagement with the needle seal, to retain the needle against the rearward bias of the spring 855. Specifically, the retaining collar 850 has an internal diameter that is the substantially the same or less than the combined diameter of the needle seal 835 and the thickness of the fingers 842. In this way, the fingers 842 operate like a collet to frictionally engage the needle seal.

At the end of an injection stroke, the plug 834 at the forward end of the plunger is dislodged by the needle seal 835. The opening at the forward end of the plunger 830 is larger than the diameter of the needle retainer 840 when the needle retainer is in engagement with the needle seal. Accordingly, as the plunger is displaced forwardly, the plunger advances over the needle retainer driving the retaining collar 850 forwardly. As the retaining collar 850 is displaced forwardly, the fingers 842 are released so they displace radially outwardly releasing the needle. The spring 855 then propels the needle rearwardly into the plunger so that the sharpened tip of the needle is protected against inadvertent contact, as shown in FIG. 28. In addition, the interior of the plunger adjacent the opening preferably tapers radially outwardly. The outer surface of the fingers 842 engage the inner tapered surface of the plunger to impede rearward displacement of the plunger, thereby locking the plunger in the barrel.

Ninth Device

Referring now to FIGS. 29-35 a ninth safety medical device is illustrated. The device is a fluid sampling device 910 having a retractable needle 960. The device is particularly suited for drawing samples of blood from a patient's artery.

The device 910 includes a housing 920 and a needle 960 projecting forwardly from the housing. A spring 955 biases the needle rearwardly toward a retracted position in which the sharpened tip of the needle is enclosed within the housing. A needle retainer 955, in the form of a latch that engages an aperture or socket 921 in the housing, releasably retains the needle in the extended position. The needle retainer 955 is integrally formed with a mounting stem 952 that is disposed within the housing. A piston or seal 970 is mounted on the mounting stem 952.

Figure 31:
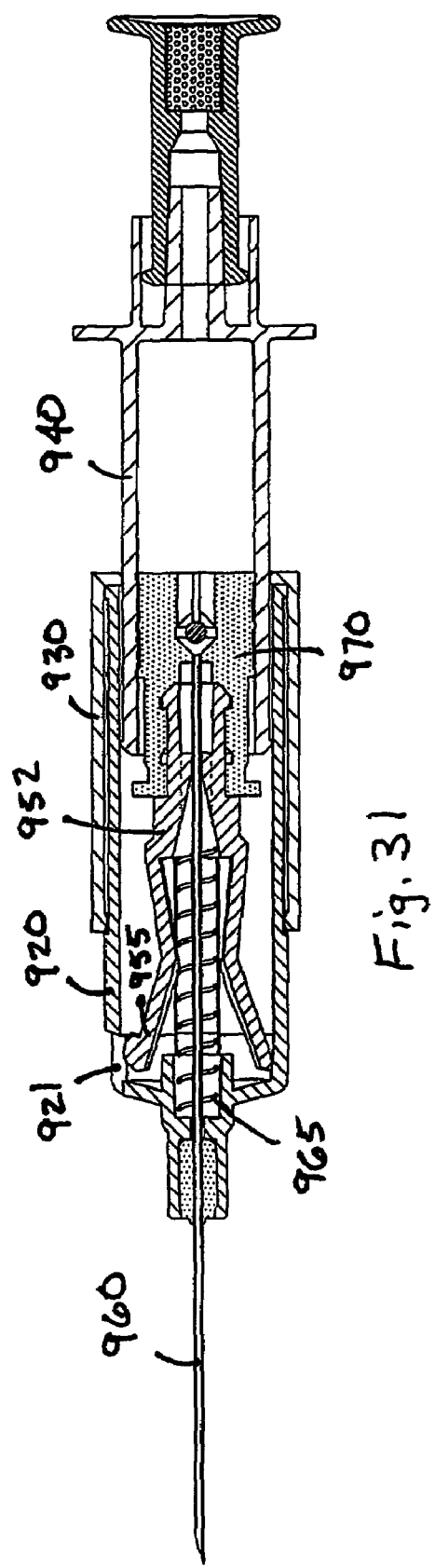
FIG. 31 is a cross-sectional view of the medical device illustrated in FIG. 30, illustrating the device after a fluid specimen has been obtained.
Figure 37:
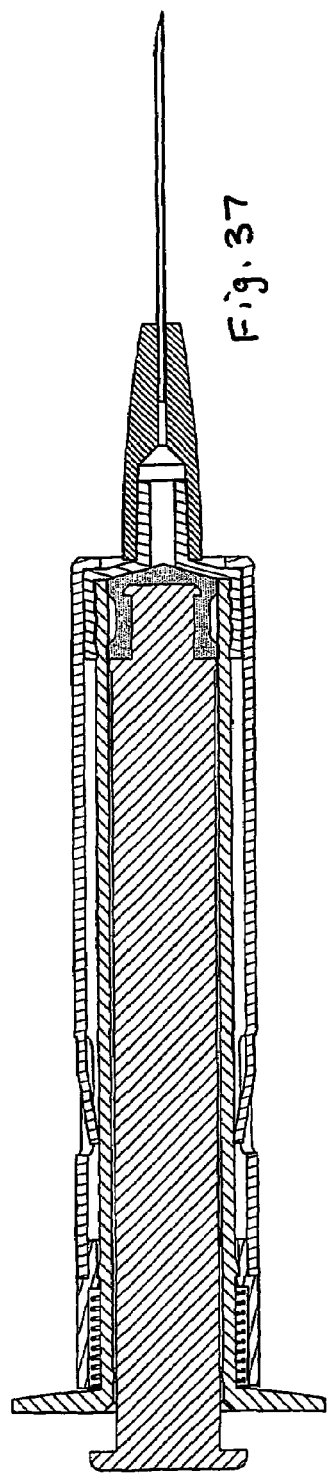
FIG. 37 is a cross-sectional view of the medical device illustrated in FIG. 36.

The piston 970 forms a fluid-tight seal with the interior of a cylindrical barrel 940 that is disposed within the interior of the housing. As shown in FIGS. 30-32, the barrel 940 is displaceable relative to the housing 920 to form a variable size fluid chamber. The fluid chamber is in fluid communication with the needle 960.

Preferably a check valve 980 is disposed within the piston 970. The check valve 980 allows fluid to flow into the fluid cavity but impedes fluid flow out of the fluid chamber through the needle 960. In the present instance, the check valve is a ball-type check valve.

Specifically, the check valve comprises an inlet port 982 for receiving fluid from the needle 960 an a discharge passage 984 for discharging fluid into the fluid chamber. A frustoconical valve seat is formed adjacent the inlet port 982. When the piston 970 is displaced rearwardly relative to the barrel, a check ball 986 seats in the valve seat to prevent fluid from flowing out of the chamber through the needle.

Retraction of the needle 960 is actuated by manually pressing a button, which disengages the needle retainer 955 latch from the housing 920. The spring 965 then propels the needle retainer 955, mounting stem 952 and barrel 940 along with the fluid sample, rearwardly. As the barrel 940 is displaced rearwardly, a circumferential flange 944 on the exterior of the forward end of the barrel engages an internal annular flange 932 that projects radially inwardly from a sleeve 930 that telescopingly engages the housing 920. As the barrel is further displaced rearwardly, the sleeve 930 is also displaced rearwardly until a pair of locking tines 957 connected to the mounting stem 952 engage locking windows 926 in the housing, which impedes further rearward movement of the sleeve and barrel, as well as the needle and mounting stem. Preferably, the locking tines 957 engage axial alignment grooves 925 in the interior of the housing, which prevent the stem 952 from rotating relative to the housing during retraction. The telescoping sleeve 930 permits usage of a shorter housing, while providing a sufficiently long enclosure for containing the used needle.

Figure 34:
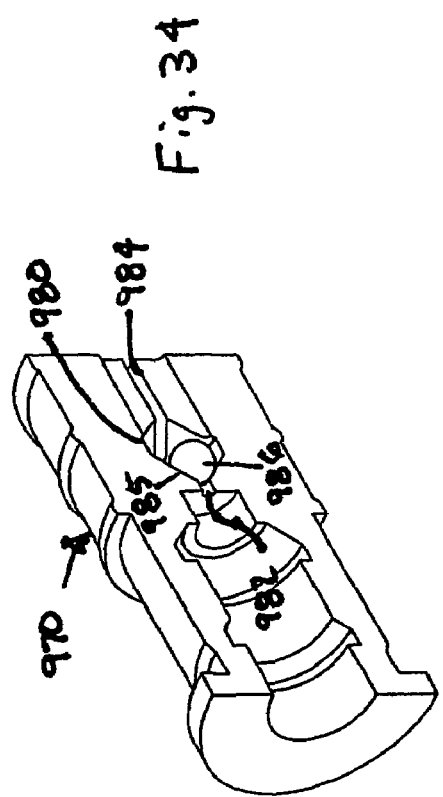
FIG. 34 is an enlarged perspective view of a piston of the device illustrated in FIG. 30.

Referring now to FIGS. 33 and 34, after the needle 960 is retracted, the fluid can be expelled from the fluid chamber in the barrel 940. Specifically, the rearward end of the barrel has a reduced diameter opening through which the fluid can be expelled. The rearward end of the barrel forms a connector 942, such as a Luer fitting for cooperating with a diagnostic device such as a blood gas analyzer. The opening in the rearward end of the barrel is sealed by a vent cap 945. The vent cap 945 engages the Luer fitting to form a fluid-tight seal. In addition, the vent cap includes a porous plug 948 that permits air to flow out of the barrel, and prevents blood from leaking out of the opening at the rear of the barrel. In this way, a blood sample can be withdrawn and maintained in a sealed condition and injected into a diagnostic device without contamination by air.

Tenth Device

Referring to FIGS. 36-40, a tenth safety medical device is illustrated. The device 1010 is a syringe having a shield 1040 for covering the needle after use is illustrated. The shield 1040 circumscribes the barrel 1020 of the syringe. A spring 1055 biases the shield 1040 forwardly. As shown in FIG. 36A, a detent 1025 formed in the side of the barrel cooperates with a recess 1049 in the shield to retain the shield in a retracted position against the bias of the spring, so that the needle 1050 is exposed for use. The forward end of the syringe barrel is generally open.

A separate cap or nose piece 1030 is attached to the forward end of the syringe barrel. The cap has a reduced diameter opening forming a tip in the form of a Luer fitting 1032. In this way, the cap encloses the forward end of the syringe barrel so that the forward end is substantially closed.

Figure 38:
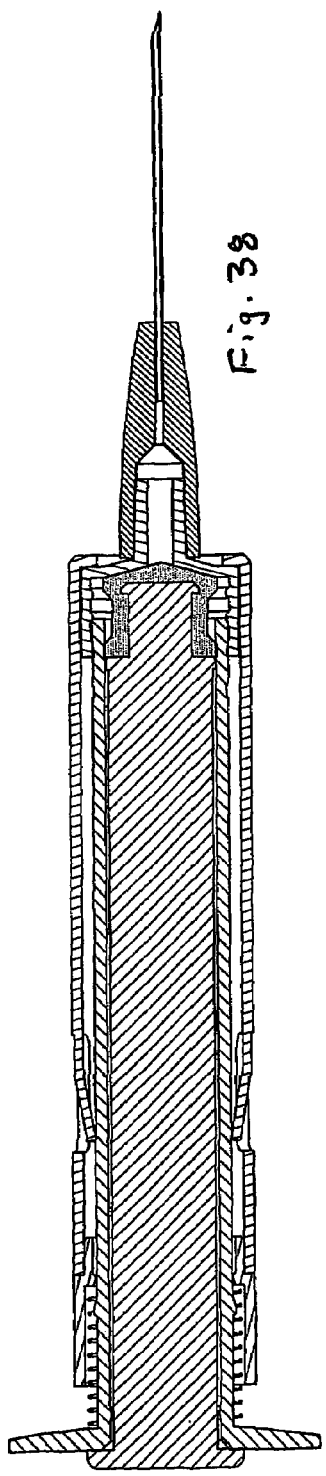
FIG. 38 is a cross-sectional view of the medical device illustrated in FIG. 36, illustrating the device just prior to advancement of the shield.
Figure 39:
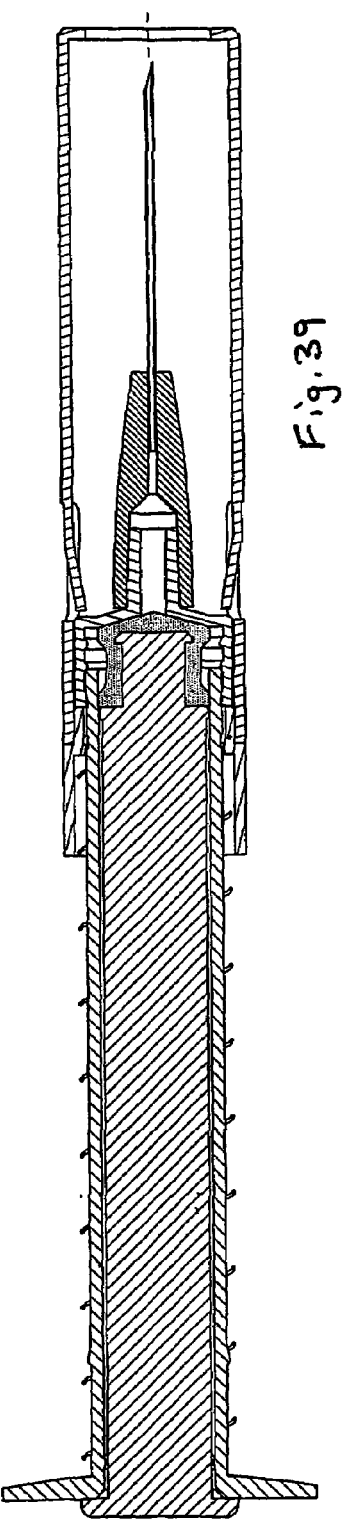
FIG. 39 is a cross-sectional view of the medical device illustrated in FIG. 36, illustrating the device after the shield is advanced.
Figure 40:
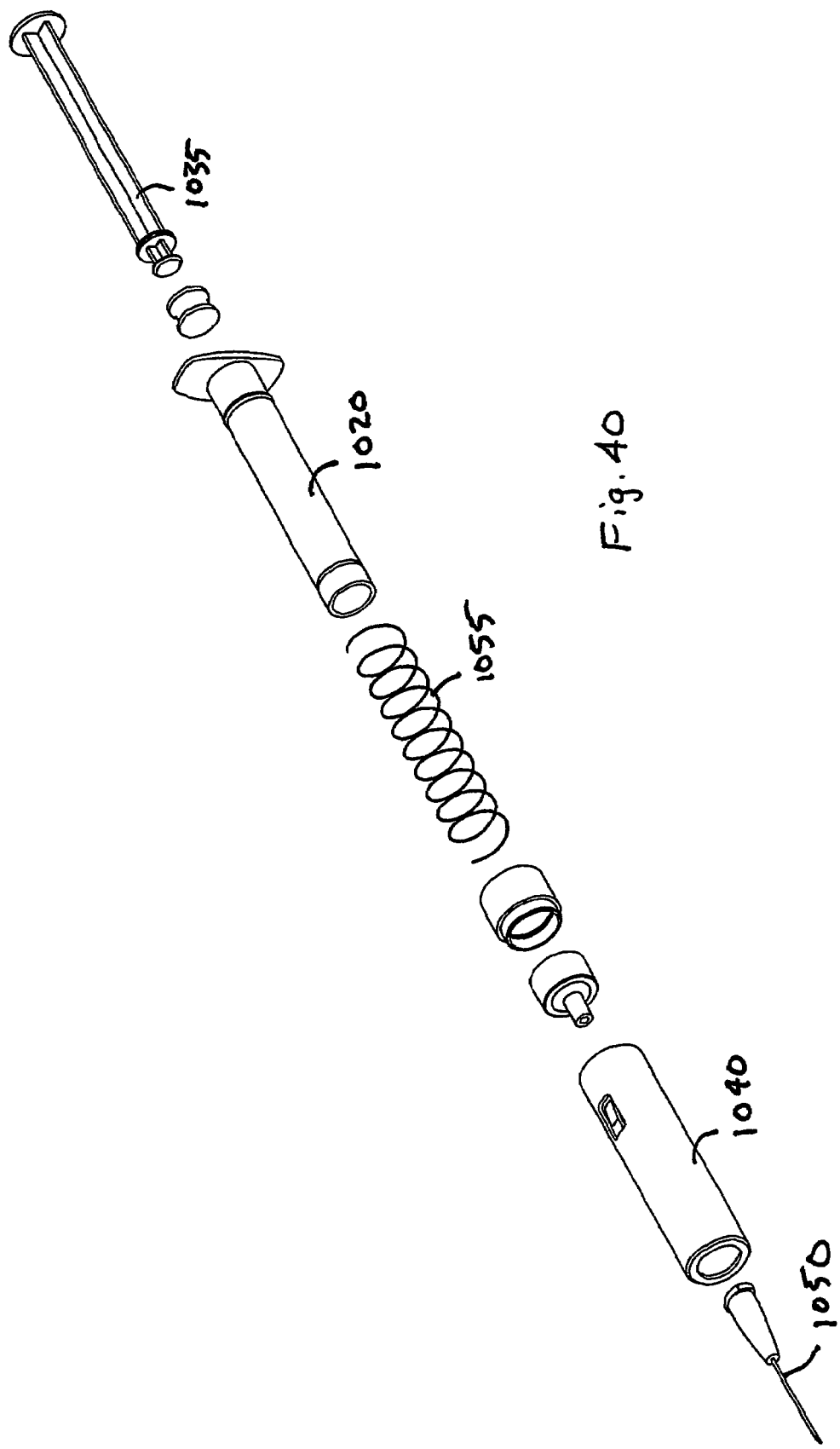
FIG. 40 is an exploded perspective view of the medical device illustrated in FIG. 36.

The cap 1030 is attached to the forward end of the barrel by a plurality of annular interference seals 1034 as shown in FIG. 36B, so that the cap or nose piece forms a snap fit connection with the syringe barrel. Referring to FIG. 38, at the end of the injection stroke, the piston at the forward end of the plunger 1035 engages the nose piece. Continued advancement of the plunger displaces the nose piece forwardly, thereby driving the shield forwardly, which in turn releases the engagement between the detent on the syringe barrel and the recess on the shield. The spring then advances the shield over the needle so that the sharpened tip of the needle is enclosed within the shield to prevent inadvertent contact with the contaminated needle. Preferably, as shown in FIG. 39, the shield includes locking tabs 1042 that prevent retraction of the shield after use.

Eleventh Device

Referring now to FIGS. 41-43, an eleventh safety medical device is illustrated. The eleventh device is a syringe. This ninth alternate embodiment is similar to the embodiments illustrated in FIGS. 21-23, which are described further above. As shown in FIG. 41, the device includes a needle retainer for releasably retaining the needle in an extended position against the bias of a spring so that the sharpened tip of the needle extends forwardly from the syringe barrel. The needle retainer is in the form of a disk having a central portion or hub that is frangibly attached to an annular outer portion. The central hub of the needle retainer is attached to the rearward end of the needle. At the end of the injection stroke, the forward end of the plunger engages the needle retainer. Further advancement of the plunger causes the outer annular portion of the needle retainer to detach from the central hub that is attached to the needle. In addition, a plug or seal at the forward end of the plunger is displaced, establishing an opening leading to the hollow interior of the plunger. After the needle retainer is fractured, the needle is released so that the spring propels the needle and attached hub rearwardly into the housing, and more specifically into the plunger. In addition, preferably the plunger includes a plurality of radially deformable resilient latching arms that provide a one-way lock to impede withdrawal of the plunger after actuation of retraction. The latches engage an annular shoulder on the interior surface of the syringe barrel.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention.

The invention claimed is:

1. A medical device, comprising:
   a hollow barrel;
   a plunger displaceable within the barrel to eject fluid from the barrel;
   a needle assembly, comprising:
      a needle having a sharpened tip, and
      a needle hub fixedly attached to the needle,
         wherein the needle assembly is operable between a projecting position in which the sharpened tip of the needle projects forwardly from the barrel and a retracted position in which the sharpened tip is retracted rearwardly;
   a needle carrier in the barrel that is connectable with the needle hub,
      wherein the needle carrier is positioned between the plunger and the needle hub, wherein a pin radially extends from the needle carrier;
   means for biasing the needle carrier rearwardly;
   means for releasably retaining the needle carrier against the bias of the biasing means, wherein the means for releasably retaining the needle carrier comprises a pin slot that is diagonal relative to axis of the needle and wherein the means for releasably retaining the needle carrier is located within the barrel;
   wherein, upon pushing the rearward end of the plunger forwardly after ejection of fluid from the barrel, the plunger causes the needle carrier to rotate such that the pin moves relative to the pin slot to enable the means for releasably retaining the needle carrier to release the needle carrier, so that the biasing means displaces the needle carrier rearwardly until the sharpened tip of the needle is shielded within the barrel.

2. The medical device of claim 1 comprising means for locking the plunger in a rearward position after the needle is retracted.

3. The medical device of claim 1 wherein the needle hub comprises a first connector and the needle carrier comprises a second connector cooperable with the first connector for attaching the needle assembly to the needle carrier.

4. The medical device of claim 1 comprising means for providing a fluid-tight seal between the barrel and the needle carrier.

5. The medical device of claim 1 wherein the biasing means is disposed between the needle carrier and the means for releasably retaining the needle carrier.

6. The medical device of claim 1 comprising means for circumferentially aligning the means for releasably retaining the needle carrier.

7. A medical device, comprising:
   a hollow barrel;
   a plunger displaceable within the barrel to eject fluid from the barrel;

a needle assembly, comprising:
   a needle having a sharpened tip, and
   a needle hub fixedly attached to the needle,
      wherein the needle assembly is operable between a projecting position in which the sharpened tip of the needle projects forwardly from the barrel and a retracted position in which the sharpened tip is retracted rearwardly;
a needle carrier in the barrel that is connectable with the needle hub,
   wherein the needle carrier is positioned between the plunger and the needle hub, wherein a pin radially extends from the needle carrier;
a coil spring positioned to bias the needle carrier rearwardly;
a collar operable to releasably retain the needle carrier against the bias of the coil spring, wherein the collar comprises a pin slot that is diagonal relative to axis of the needle and wherein the collar is located within the barrel;
wherein, upon pushing the rearward end of the plunger forwardly after ejection of fluid from the barrel, the plunger causes the needle carrier to rotate such that the pin moves relative to the pin slot to enable the collar to release the needle carrier, so that the coil spring displaces the needle carrier rearwardly until the sharpened tip of the needle is shielded within the barrel.

8. The medical device of claim 7 comprising a lock for locking the plunger in a rearward position after the needle is retracted.

9. The medical device of claim 7 wherein the needle hub comprises a first connector and the needle carrier comprises a second connector cooperable with the first connector for attaching the needle assembly to the needle carrier.

10. The medical device of claim 7 comprising a seal for providing a fluid-tight seal between the barrel and the needle carrier.

11. The medical device of claim 7 wherein the coil spring is disposed between the needle carrier and the collar.

12. The medical device of claim 7 comprising an alignment element for circumferentially aligning the collar.

* * * * *

UNITED STATES PATENT AND TRADEMARK OFFICE
CERTIFICATE OF CORRECTION

PATENT NO.        : 7,329,238 B2                              Page 1 of 1
APPLICATION NO. : 10/149172
DATED             : February 12, 2008
INVENTOR(S)       : Thor R. Halseth et al.

It is certified that error appears in the above-identified patent and that said Letters Patent is hereby corrected as shown below:

In the second column of the Title page, Item [56] replace the first line below the heading FOREIGN PATENT DOCUMENTS, which reads "EP  0 565 882  10/1993", with --EP  0 566 882  10/1993--.

Signed and Sealed this

Seventh Day of July, 2009

JOHN DOLL
*Acting Director of the United States Patent and Trademark Office*